(12) United States Patent
Tewari et al.

(10) Patent No.: US 10,820,539 B2
(45) Date of Patent: *Nov. 3, 2020

(54) MICROPROPAGATION OF BLACK BARHEE DATE PALM

(71) Applicant: Phoenix Agrotech, LLC, Santa Ana, CA (US)

(72) Inventors: Krishna Tewari, Irvine, CA (US); Anthony Fortier, Irvine, CA (US)

(73) Assignee: Phoenix Agrotech, LLC, Santa Ana, CA (US)

( * ) Notice: Subject to any disclaimer, the term of this patent is extended or adjusted under 35 U.S.C. 154(b) by 87 days.

This patent is subject to a terminal disclaimer.

(21) Appl. No.: 15/754,901

(22) PCT Filed: Aug. 25, 2016

(86) PCT No.: PCT/US2016/048775
§ 371 (c)(1),
(2) Date: Feb. 23, 2018

(87) PCT Pub. No.: WO2017/035397
PCT Pub. Date: Mar. 2, 2017

(65) Prior Publication Data
US 2018/0279571 A1 Oct. 4, 2018

Related U.S. Application Data

(60) Provisional application No. 62/209,816, filed on Aug. 25, 2015, provisional application No. 62/210,352, filed on Aug. 26, 2015.

(51) Int. Cl.
*A01H 4/00* (2006.01)

(52) U.S. Cl.
CPC .............. *A01H 4/005* (2013.01); *A01H 4/008* (2013.01)

(58) Field of Classification Search
None
See application file for complete search history.

(56) References Cited

U.S. PATENT DOCUMENTS

| 2018/0242542 A1* | 8/2018 | Tewari | A01H 4/005 |
| 2018/0242543 A1* | 8/2018 | Tewari | A01H 4/005 |
| 2018/0352765 A1* | 12/2018 | Tewari | A01H 4/005 |
| 2019/0110419 A1 | 4/2019 | Tewari et al. | |

FOREIGN PATENT DOCUMENTS

| EP | 3340773 A1 | 7/2018 |
| EP | 3340774 A1 | 7/2018 |
| EP | 3340775 A1 | 7/2018 |
| EP | 3340776 A1 | 7/2018 |
| EP | 3340777 A1 | 7/2018 |
| IL | 257715 | 4/2018 |
| IL | 257716 | 4/2018 |
| IL | 257717 | 4/2018 |
| IL | 257718 | 4/2018 |
| IL | 257719 | 4/2018 |
| WO | 2017035330 A1 | 3/2017 |
| WO | 2017035346 A1 | 3/2017 |
| WO | 2017035379 A1 | 3/2017 |
| WO | 2017035385 A1 | 3/2017 |
| WO | 2017035397 A1 | 3/2017 |

OTHER PUBLICATIONS

Castellar et al (In vitro propagation and establishment of callus and cell suspension cultures of *Petiveria alliacea* L., a valuable medicinal plant. Journal of Medicinal Plants Research vol. 5(7), pp. 1113-1120, Apr. 4, 2011)az (Year: 2011).*
Kaabi et al (Effect of Auxins and Cytokinins on the in Vitro Production of Date Palm (*Phoenix dactylifera* L.) Bud Generative Tissues and on the Number of Differentiated Buds. Published Dec. 26, 2012 on https://www.pubhort.org) (Year: 2012).*
Khan et al (Direct Shoot Regeneration System for Date Palm (*Phoenix dactylifera* L.) CV. Dhakki as a Means of Micropropagation. Pak. J. Bot., 44(6): 1965-1971, 2012) (Year: 2012).*
Rad et al (Comparison of vegetative buds formation in two date palm cultivars, Medjool and Mazafati through direct organogenesis. Intl J Farm & Alli Sci. vol. 4 (6): 549-553, Jun. 2015). (Year: 2015).*
Cao et al (Identification of Date Cultivars in California Using AFLP Markers. Hortscience 37(6):966-968. 2002) (Year: 2002).*
International Preliminary Report on Patentability for PCT/US2016/048640 dated Mar. 8, 2018, 11 pages.
International Preliminary Report on Patentability for PCT/US2016/048685 dated Mar. 8, 2018, 12 pages.
International Preliminary Report on Patentability for PCT/US2016/048743 dated Mar. 8, 2018, 11 pages.
International Preliminary Report on Patentability for PCT/US2016/048756 dated Mar. 8, 2018, 11 pages.
International Preliminary Report on Patentability for PCT/US2016/048775 dated Mar. 8, 2018, 11 pages.
International Search Report and Written Opinion for PCT/US2016/048640 dated Nov. 14, 2016, 16 pages.
Al-Khalifah et al., Micropropagation of Date Palms, 2012, retrieved from: "http://www.apcoab.org/uploads/files/1352364901micropropagation_datapalms_pub.pdf" on Oct. 24, 2016, 68 pages.
Kahn et al., Direct Shoot Regeneration System for Date Palm (*Phoenix dactylifera* L.) CV. Dhakki as a Means of Micropropagation, 2012, retrieved from: "http://www.pakbs.org/pjbot/PDFs/44(6)/21.pdf", 8 pages.

(Continued)

*Primary Examiner* — Soren Harward
*Assistant Examiner* — Wayne Zhong
(74) *Attorney, Agent, or Firm* — Seth D. Levy; Nixon Peabody LLP

(57) ABSTRACT

Disclosed herein are media, kits, systems and methods for achieving micropropagation of a Black Barhee date palm on a commercially relevant scale. Compositions and methods for each stage of micropropagation, including initiation, elongation, and rooting are disclosed in the present application. Also disclosed are conditions for harvesting and sterilizing explant tissue for micropropagation.

10 Claims, 10 Drawing Sheets

(56) References Cited

OTHER PUBLICATIONS

Al Kaabi et al., Effect of Auxins and Cytokinins on the In Vitro Production of Date Palm (*Phoenix Dactylifera* L.) Bud Generative Tissues and on the Number of Differentiated Buds, 2006, retrieved from: "http://www.pubhort.org/datepalm/datepalm2/datepalm2_6.pdf" on Oct. 25, 2016, 40 pages.

Bekheet, Direct Organogenesis of Date Palm (*Phoenix dactylifera* L.) for Propagation of True-to-Type Plants, Scientia Agriculturae, 2013, retrieved from: "http://pscipub.com/Journals/Data/Jlist/Scientia Agriculturae/2013/Volume4/Issue3/5.pdf" on Oct. 24, 2016, 8 pages.

Jain et al., Date Palm Biotechnology, 2011, retrieved from: "http://webagris.inra.org.ma/doc/abahmane201101.pdf" on Oct. 24, 2016, 30 pages.

Khierallah et al., Micropropagation of Date Palm (*Phoenix dactylifera* L.) var. Maktoom through Direct Organogenesis, 2007, pp. 213-224.

Mazri et al., An improved method for micropropagation and regeneration of date palm (*Phoenix dactylifera* L.), Journal of Plant Biochemistry and Biotechnology, 2012, vol. 22, pp. 176-184.

Al'Utbi et al., The effect of IAA and Other Auxins on the Growth of Date Palm (*Phoenix dactylifera* L.) Shoot Tips and Callus, 2014, retrieved from: "http://www.iasj.net/iasj?func=fulltext&ald=5468" on Oct. 24, 2016, 14 pages.

Almusawi et al., Induction of direct somatic embryogenesis in date palm (*Phoenix dactylifera* L.) cv. Hellawi, AAB Bioflux Advances in Agriculture & Botanics—International Journal of the Bioflux Society 2015, retrieved from: "http://www.aaa.bioflux.com.ro/docs/2015.80-89.pdf" on Oct. 24, 2016, 10 pages.

Kriaa et al., The date palm (*Phoenix dactylifera* L.) micropropagation using completely mature female flowers, Comptes Rendus Biologies, 2012, vol. 335, pp. 194-204.

Aslam et al., In Vitro Micropropagation of "Khalas" Date Palm (*Phoenix dactylifera* L.), An Important Fruit Plant, Journal of Fruit and Ornamental Plant Research, 2008, retrieved from: "http://www.insad.pl/files/journal_pdf/journal2009/vol17(1)2009/Full2 2009_1_.pdf" on Oct. 19, 2016, 14 pages.

Mazri et al., Micropropagation of Date Palm: A Review, Cell & Developmental Biology, 2015, vol. 04, 6 pages.

Abdulwahed, Identification of the effect of different types of activated charcoal and sucrose on multiplication shoots of date palm phenixdactylifera L.C.v. sufedy in vitro, Journal of Horticulture and Forestry, 2013, retrieved from: "http://www.academicjournals.org/journal/JHF/article-full-text-pdf/5C226CF3361", 8 pages.

International Search Report and Written Opinion for PCT/US2016/048685 dated Nov. 9, 2016, 16 pages.

International Search Report and Written Opinion for PCT/US2016/048743 dated Nov. 11, 2016, 16 pages.

International Search Report and Written Opinion for PCT/US2016/048756 dated Nov. 7, 2016, 16 pages.

International Search Report and Written Opinion for PCT/US2016/048775 dated Nov. 11, 2016, 16 pages.

Johnson et al., Seedling Date Palms (*Phoenic dactylifera* L.) as Genetic Resources, Emir J. Food Agric., 2013, vol. 25(11), pp. 809-830.

Kader et al., Harvesting and Postharvest Handling of Dates, Project on the Development of Sustainable Date Palm Production Systems in the GCC countries of the Arabian peninsula, ICARDA, pp. 1-15, 2009.

\* cited by examiner

MICROPROPAGATION OF BLACK BARHEE DATE PALM

CROSS-REFERENCE TO RELATED APPLICATIONS

This application is the National Phase of International Application PCT/US2016/048775, filed Aug. 25, 2016, which designated the United States and that International Application was published under PCT Article 21(2) in English. This application claims priority under 35 U.S.C. § 119(e) to U.S. Provisional Application No. 62/209,816 filed Aug. 25, 2015 and U.S. Provisional Application No. 62/210,352 filed Aug. 26, 2015, the contents of which are incorporated herein by reference in their entirety.

FIELD OF THE INVENTION

The invention generally relates to media, kits, systems and methods for achieving micropropagation of Black Barhee date palms.

BACKGROUND

The following description includes information that may be useful in understanding the present invention. It is not an admission that any of the information provided herein is prior art or relevant to the presently claimed invention.

The date tree is dioecious, i.e., female and male flowers develop on different individuals. To produce fruits, the female trees have to be pollinated with pollen produced by the male tree. The fruits contain viable seeds, but propagation by seed is time-consuming due to heterozygosity and resulting segregation. Conventional propagation is carried out through vegetative cloning via so-called date palm offshoots (suckers). However, the number of offshoots produced by individual date palms is limited and production restricted to early developmental stages. The number of trees required to replace destructed, diseased or newly planned orchards cannot be nearly produced through conventional vegetative cloning. In addition, cloning through natural propagules usually does not eliminate pathogens present in the parent plant but rather may lead to their accumulation. Only an appropriate in-vitro cloning (micropropagation) technique with strong multiplication results has the potential to deliver enough healthy trees for a timely relief of the shortage. In troubled areas, such a relief would significantly contribute to the amelioration of hunger and desertification and would contribute to society building and pacification. In areas with more intact infrastructure, newly planted orchards can be of significant economic importance.

One variety of date which is considered especially important to the date industry is Black Barhee (also known as 8-Ball). Developed by Ben Laflin, Jr., Black Barhee is the product of a pistillate Barhee crossed with a fourth-generation-backcrossed staminate Medjool. The staminate Medjool was a product of the breeding program at the USDA Date and Citrus Station in Indio, Calif. Laflin obtained the staminate Medjool when the station closed in 1980, and Black Barhee first fruited in the 1990s. A very dark, nearly black date, Black Barhee is noted for its soft, smooth flesh and pleasing flavor. The Black Barhee date palm is intermediate in appearance between the two parent varieties. Black Barhee date palm lacks characteristic wings or ridges on the seed, belying its Medjool parentage. Although it produces significantly more offshoots than Benji, many offshoots of Black Barhee are high on the trunk.

A non-limiting description of characteristics of Black Barhee date palm fruit is provided herein. One of skill in the art would realize that the description could vary somewhat for various reasons.
Fruit—Khalal red; rutab and tamar very dark brown, nearly black, with glaucous bloom lending a somewhat purplish cast; broadly ovate; 33-40 mm×26-30 mm; skin medium, shrinking with and adhering to flesh in irregular folds; flesh moderately soft, smooth with little rag; flavor pleasing; ripening midseason.
Seed—Brownish with some areas of gray; oblong-elliptic, broadest at or slightly distal of middle, apex rounded and prominently mucronate, base pointed; 16-24 mm×8-10 mm; germ pore central; furrow wide, shallow.

The difficulties encountered in the micropropagation of date palm, including Black Barhee, are the various physiological stages of offshoots coming from extreme climatic environments, the physiological shock produced by the rough harvest techniques for offshoots and flowers, the equally rough isolation technique for the apical explant, the high incidences of material contamination, the polyphenol production and peroxidation of explants and problems related to hyperhydricity, dormancy, and positional bud effects (topophysis). There is a need in the art for media, kits, systems and methods that overcome these difficulties, and allow for commercial-scale mass-cloning of date palms, including Black Barhee.

SUMMARY OF THE INVENTION

In various embodiments, the invention teaches a method for micropropagating a Black Barhee date palm. In some embodiments, the method includes applying a first medium in vitro to a Black Barhee date palm explant tissue that includes meristematic cells, at least until a shoot is initiated, wherein the first medium includes: (a) 6-(gamma-gamma-dimethylallylamino)-purine (2-ip), 6-Benzylaminopurine (BAP) and Naphthoxyacetic acid (NOA); or (b) 2,4-Dichlorophenoxyacetic acid (2,4-D), 6-(gamma-gamma-dimethylallylamino)-purine (2-iP) and kinetic (KIN); or (c) 6-Benzylaminopurine (BAP), kinetic (KIN), and 1-Naphthaleneacetic acid (NAA); and applying a second medium in vitro to the initiated shoot, wherein the second medium includes 6-Benzylaminopurine (BAP).

In some embodiments, the invention teaches a method for micropropagating a Black Barhee date palm that includes applying a first medium in vitro to a Black Barhee date palm explant tissue that includes meristematic cells, until a shoot is initiated, wherein the first medium includes: (a) 6-(gamma-gamma-dimethylallylamino)-purine (2-ip), 6-Benzylaminopurine (BAP) and Naphthoxyacetic acid (NOA); or (b) 2,4-Dichlorophenoxyacetic acid (2,4-D), 6-(gamma-gamma-dimethylallylamino)-purine (2-iP) and kinetic (KIN); or (c) 6-Benzylaminopurine (BAP), kinetic (KIN), and 1-Naphthaleneacetic acid (NAA). In some embodiments, the first and/or second media further includes charcoal. In some embodiments, the first medium further includes any of about 25%, about 50%, about 75%, about 90% or 100% of Murashige and Skoog standard concentration of salts.

In various embodiments, the invention teaches a method for micropropagating a Black Barhee date palm that includes applying a medium in vitro to an initiated Black Barhee date palm shoot derived from an explant, wherein the medium includes 6-Benzylaminopurine (BAP). In some embodiments, the medium further includes any of about 25%, about 50%, about 75%, about 90% or 100% of Murashige and Skoog standard concentration of salts. In certain embodiments, the Black Barhee date palm is a male. In some embodiments, the Black Barhee date palm is a female. In certain embodiments, the Black Barhee date palm explant includes plant tissue from an offshoot of a Black Barhee date palm. In some embodiments, the Black Barhee date palm explant includes plant tissue from a flower, a leaf, or a bud of a Black Barhee date palm.

In various embodiments, the invention teaches a medium that includes the constituents of PAE-1, PAE1-M, PAE-9, PAE-21, PAE-71, PAE-19 or PAE-7.

In various embodiments, the invention teaches a kit for micropropagating a Black Barhee date palm. In some embodiments, the kit includes one or more media that includes the constituents of a medium selected from PAE-1, PAE-1M, PAE-71, PAE-9, PAE-19, PAE-21 and PAE-7. In some embodiments, the kit further includes a tissue of a Black Barhee date palm. In some embodiments, the tissue includes plant tissue from an offshoot, a flower, a leaf, or a bud of the Black Barhee date palm. In some embodiments, the kit further includes instructions for the use of the one or more media for the purpose of micropropagating the Black Barhee date palm.

In various embodiments, the invention teaches a Black Barhee date palm resulting from any of the methods described above.

In various embodiments, the invention teaches a Black Barhee date palm tissue resulting from any of the methods described above.

In various embodiments, the invention teaches a Black Barhee date palm cell resulting from any of the methods described above.

In various embodiments, the invention teaches a Black Barhee date palm plant resulting after exposing a tissue or a cell of a Black Barhee date palm to media that includes the constituents of a medium selected from PAE-1, PAE1-M, PAE-9, PAE-71, PAE-19, PAE-21 and PAE-7. In some embodiments, the origin of the tissue is an offshoot, a flower, a leaf, or a bud.

In various embodiments, the invention teaches a Black Barhee date palm tissue resulting after exposing a tissue or a cell of a Black Barhee date palm to media that includes the constituents of a medium selected from PAE-1, PAE-1M, PAE-71, PAE-9, PAE-21, and PAE-7. In various embodiments, the origin of the tissue of the Black Barhee date palm is an offshoot, a flower, a leaf, or a bud.

In various embodiments, the invention teaches a Black Barhee date palm plant cell resulting from exposing a tissue or a cell of a Black Barhee date palm to media that includes the constituents of a medium selected from PAE-1, PAE-1M, PAE-71, PAE-9, PAE-21, PAE-19 and PAE-7. In certain embodiments, the tissue or the cell originates from a callus formed on an explant of a Black Barhee date palm. In some embodiments, the explant includes tissue from a flower, a bud, a leaf, or an offshoot of a Black Barhee date palm.

In various embodiments, the invention teaches a Black Barhee date palm plant resulting from exposing a globule of a callus of a Black Barhee date palm explant to a medium comprising the constituents of medium selected from the group consisting of PAE-1, PAE-1M, PAE-9, PAE-19, PAE-21, and PAE-7, wherein a starting material from which the callus is formed is a flower, a bud, a leaf, or an offshoot of a Black Barhee date palm.

BRIEF DESCRIPTION OF THE DRAWINGS

Exemplary embodiments are illustrated in the referenced figures. It is intended that the embodiments and figures disclosed herein are to be considered illustrative rather than restrictive.

DESCRIPTION OF THE INVENTION

Figure 1:
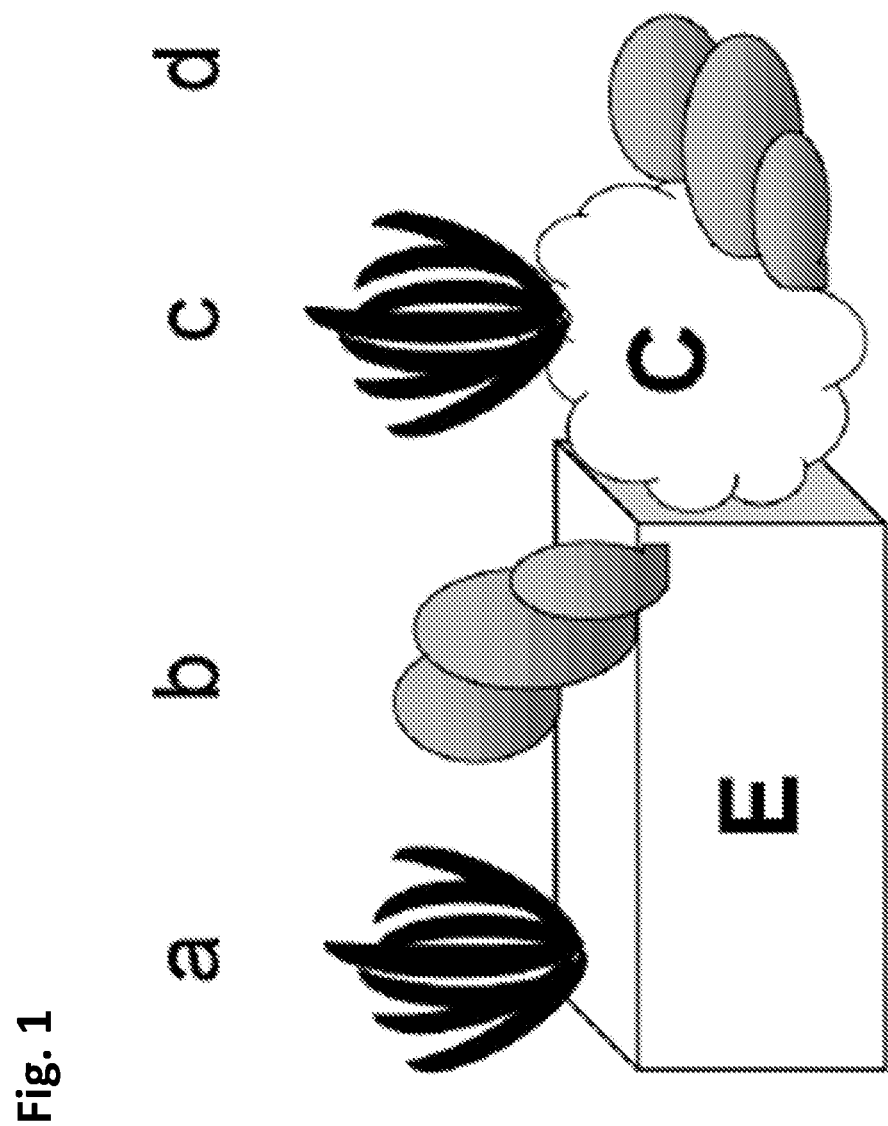
FIG. 1 depicts, in accordance with various embodiments of the invention, a schematic representation of the 4 general plant regeneration pathways of explants (a) direct organogenesis, (b) direct embryogenesis, (c) indirect organogenesis and (d) indirect embryogenesis. C=callus; E=explant.
Figure 2:
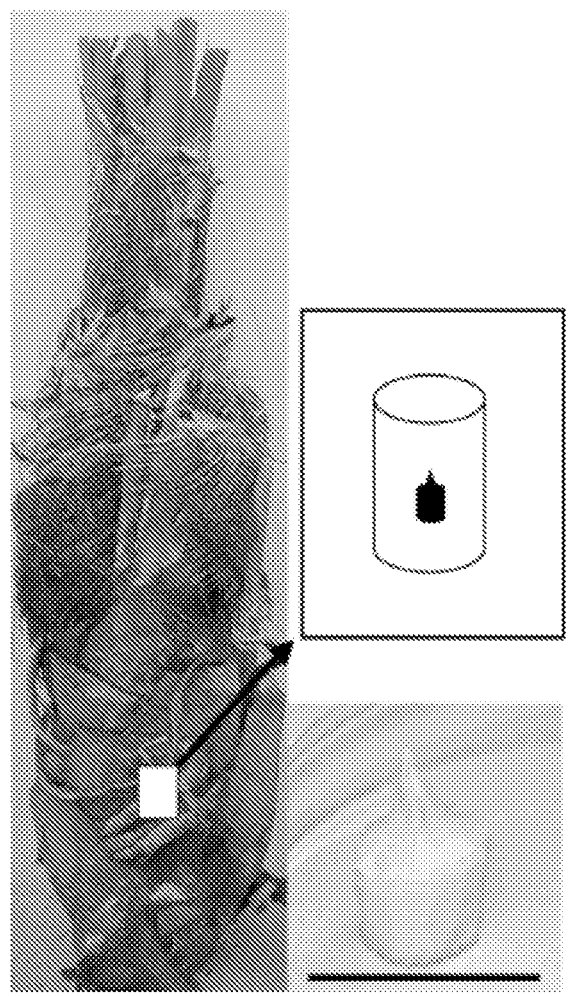
FIG. 2 depicts, in accordance with various embodiments of the invention, an offshoot, weighing approximately 18 pounds (3 feet in length), with the position where the shoot bud is situated in the core of the offshoot marked (white box). A cylindrical piece of approximately 6 cm by 8 cm, containing the shoot bud in its center, is excised, sterilized and further stripped under aseptic conditions until the bud (triangle) is uncovered. Offshoot removal and the initial steps of explant isolation require forceful manipulations. Great care must be taken not to injure the core during these steps. Bar=10 mm.
Figure 3:
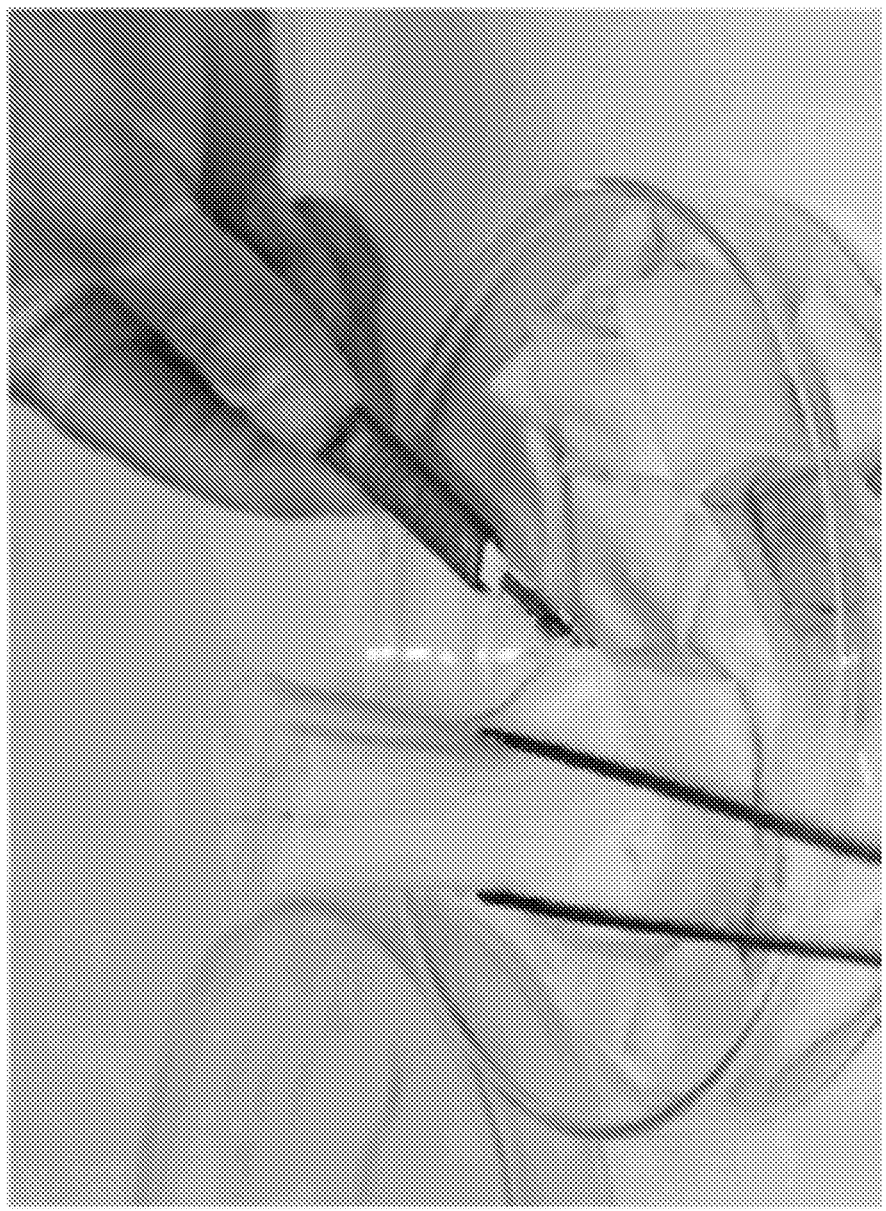
FIG. 3 depicts, in accordance with various embodiments of the invention, tissue culture steps are performed in a laminar flow hood to create sterile working conditions. Prior to further excision, the isolated offshoot core is subjected to chemical sterilization. The cylindrical piece is preferably large enough not to allow the damaging chemicals (bleach, alcohol) to penetrate the fragile bud. The picture illustrates the further removal of leaves from the cylinder.
Figure 4:
FIG. 4 depicts, in accordance with various embodiments of the invention, a bud (front, see also FIG. 2) and two adjacent leaf pieces on a solidified culture medium. Explants may be considerably smaller.
Figure 5:
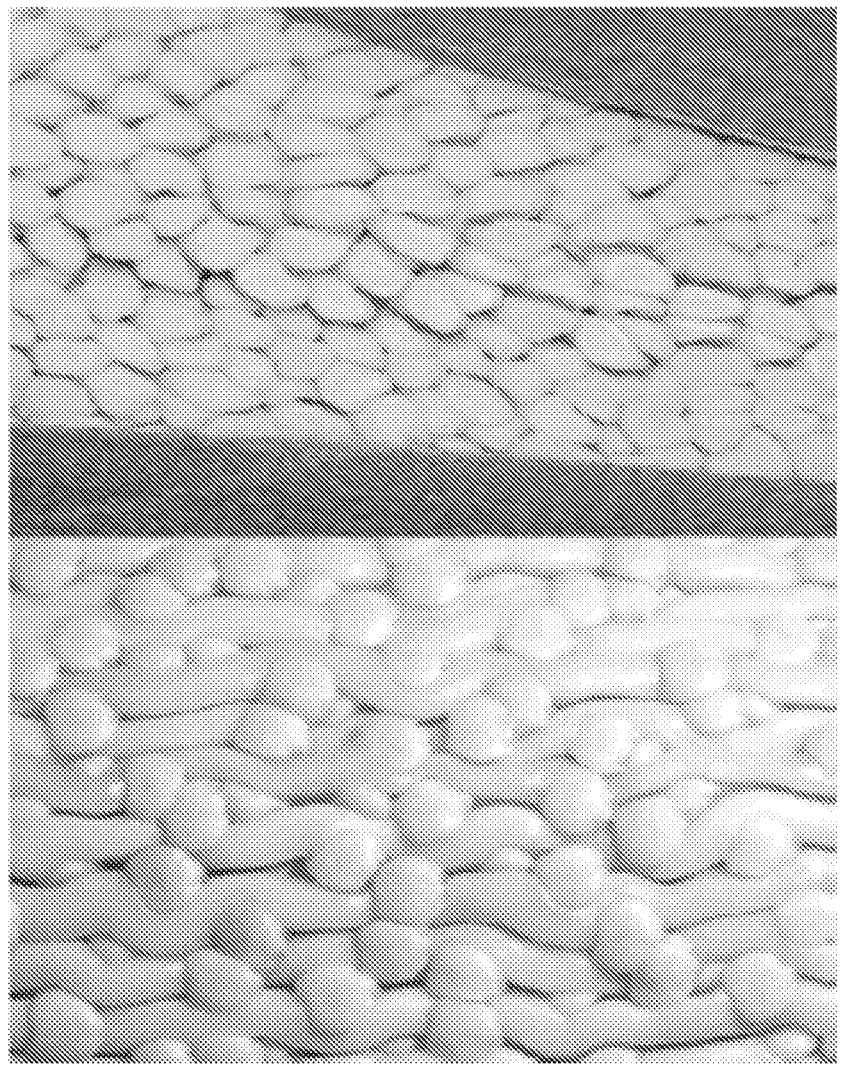
FIG. 5 depicts, in accordance with various embodiments of the invention, densely packed male (top) and female flowers (bottom) with protective sheath (spathe) cut open (brown spathe visible at top). Flowers stalks taken into tissue culture can be younger than those shown here.
Figure 6:
FIG. 6 depicts, in accordance with various embodiments of the invention, regenerating explants showing growth and greening of secondary leaf buds (organogenesis).
Figure 7:
FIG. 7 depicts, in accordance with various embodiments of the invention, regenerated date palm plant on rooting medium. The plant shown can be transferred to soil and carefully acclimatized.
Figure 8:
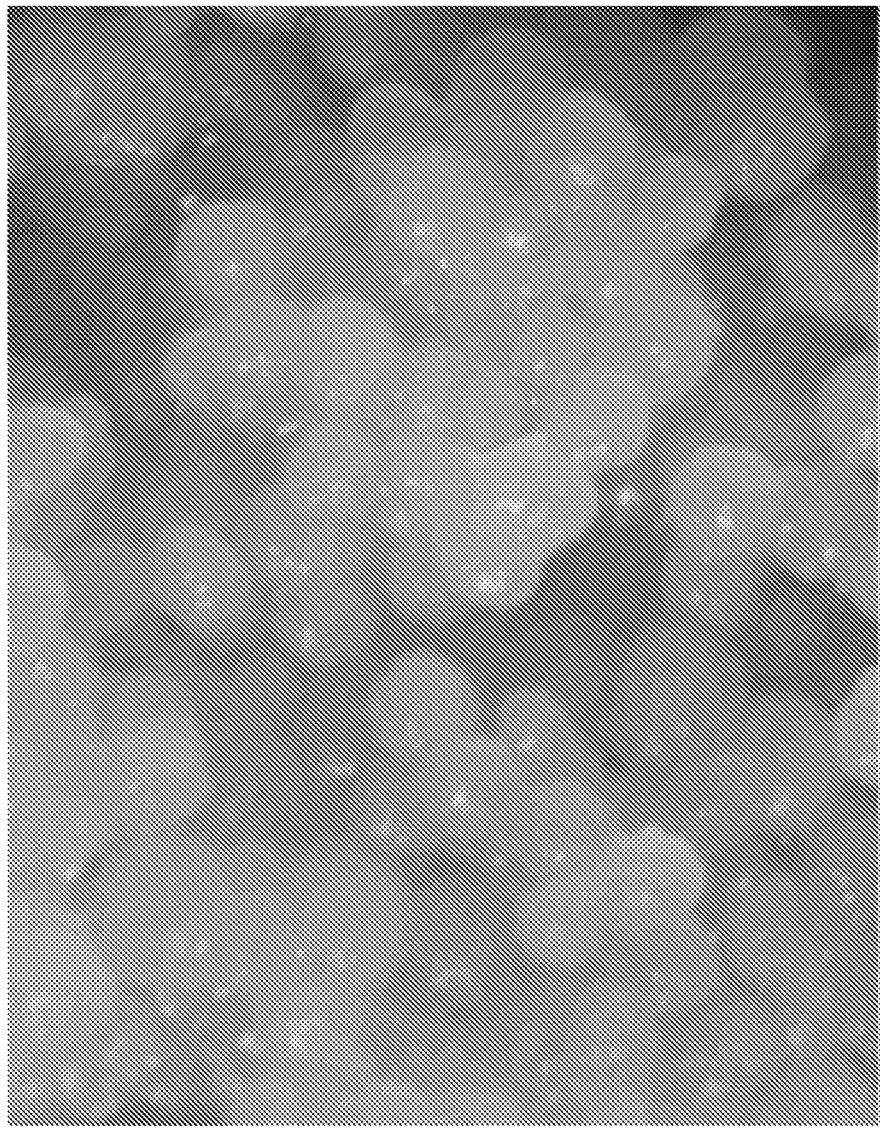
FIG. 8 depicts, in accordance with various embodiments of the invention, embryogenic callus showing numerous globular structures (early embryos) that can be further multiplied and developed into mature embryos, each one a potential date palm plant.
Figure 9:
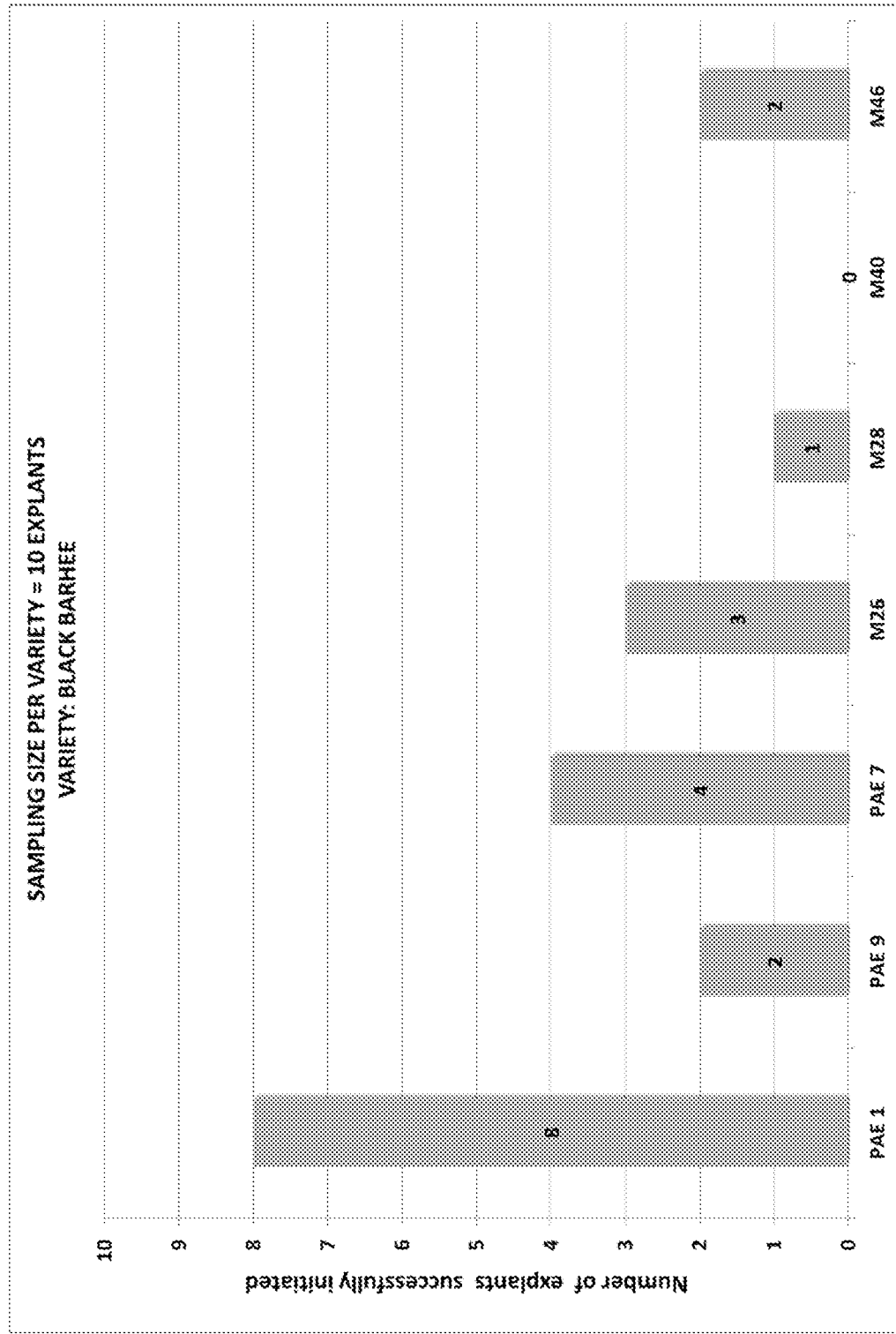
FIG. 9 depicts, in accordance with various embodiments of the invention, a bar graph indicating the number of explants of a Black Barhee date palm successfully initiated (i.e. in which a plant organ or portion thereof is initiated (i.e. begins to grow) from the explant) on each media type listed on the x-axis. A total of 10 explants were tested on each medium. PAE1 is the same as PAE-1 described herein, PAE9 is the same as PAE-9 described herein, and PAE7 is the same as PAE-7 described herein.
Figure 10:
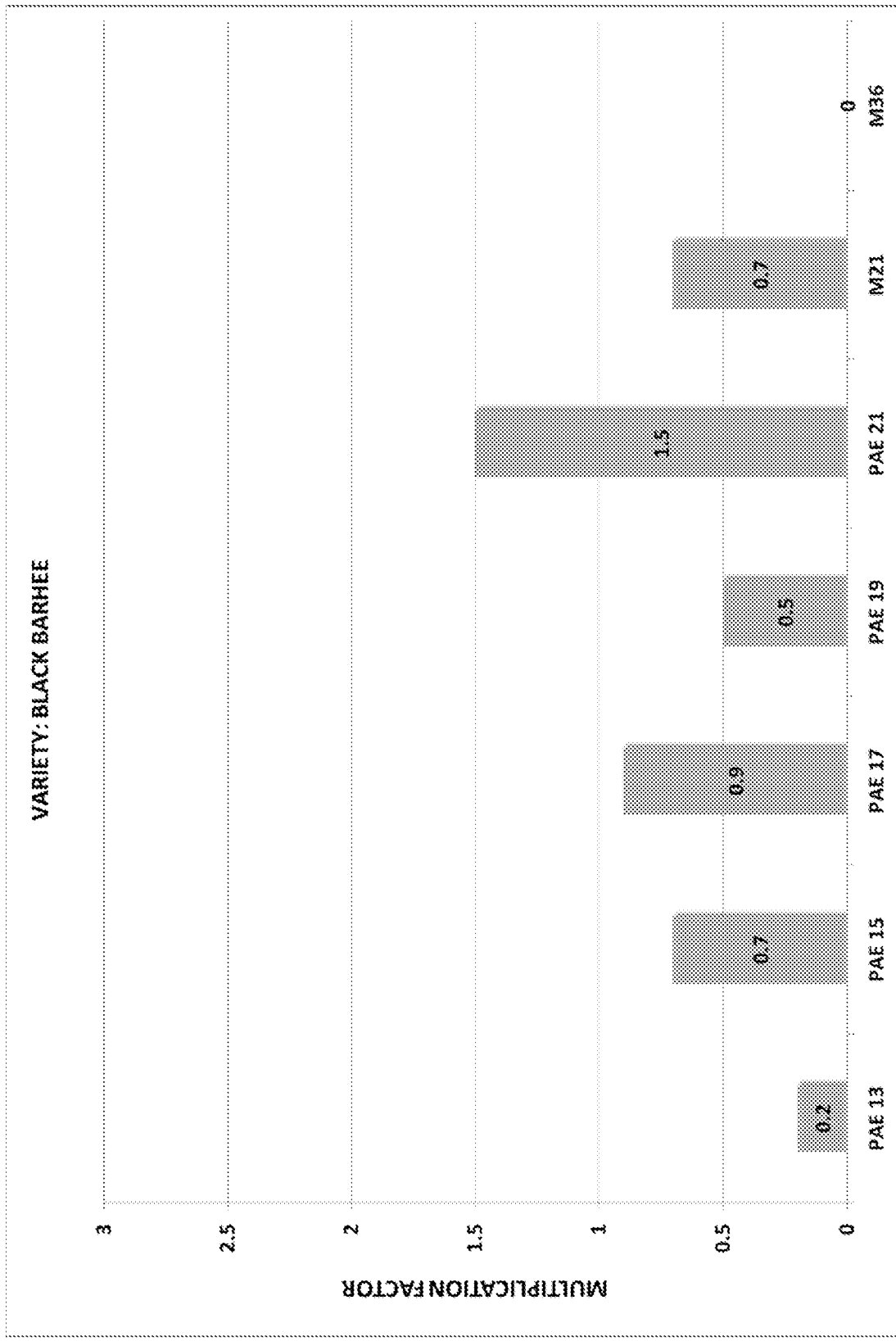
FIG. 10 depicts, in accordance with various embodiments of the invention, a bar graph indicating the multiplication factor (i.e. fold increase in number of propagules produced per 8 weeks) for each media type on which Black Barhee date palm tissue was placed, as listed on the x-axis. A total of 10 explants were tested on each medium. PAE13 is the same as PAE-13 described herein, PAE15 is the same as PAE-15 described herein, PAE17 is the same as PAE-17 described herein, PAE19 is the same as PAE-19 described herein, and PAE21 is the same as PAE-21 described herein.

All references cited herein are incorporated by reference in their entirety as though fully set forth. Unless defined otherwise, technical and scientific terms used herein have the same meaning as commonly understood by one of ordinary skill in the art to which this invention belongs. Smith, *March's Advanced Organic Chemistry Reactions, Mechanisms and Structure* 7th ed., J. Wiley & Sons (2013); Jain et al., Date Palm Biotechnology, Springer (2011); Taiz et al., *Plant Physiology and Development* 6th ed., Sinauer Associates, Inc. (2010), and Hodel, D. R. and D. V. Johnson. 2007. *Imported and American Varieties of Dates (Phoenix dactlifera)* in the United States. UC ANR Publication 3498. Oakland, Calif.: University of California will provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

As used herein, "2,4-D" means 2,4-Dichlorophenoxyacetic acid.

As used herein, "BAP" means 6-Benzylaminopurine.

As used herein, "NAA" means 1-Naphthaleneacetic acid.

As used herein, "2iP" means 6-(gamma,gamma-Dimethylallylamino)purine.

As used herein, "NOA" means Naphthoxyacetic acid.

As used herein, the term "date palm" refers to Black Barhee date palm. Both male and female Black Barhee date palms are intended to be included within the meaning of the term "date palm."

As indicated above, embodiments disclosed herein provide for the micropropagation or tissue culturing (these terms are used interchangeably herein) of Black Barhee date palms on a commercial scale. Each discrete step described below and associated with micropropagation may be utilized in conjunction with protocols other than those described herein. Thus, for example, the inventive harvesting or sterilization techniques described herein may be implemented in conjunction with methods and media different than those specifically set forth or referenced herein, and therefore represent "stand alone" contributions to the field.

Harvesting & Tissue Preparation
Physiological Quality of Donor-Plants

Preferably, offshoots are taken from a professionally managed orchard with no known infestation of Black Barhee date palm.

Explant Types

By way of non-limiting examples, explants can be isolated from offshoots, male and female flowers, or flowers from offshoots.

Physiological Quality of the Explants

Preferably, explants should be white in nature with little or no yellowish color.

Harvesting Procedure

In some embodiments, before flowers are open the inflourescence are taken with outer layers removed to expose the flowers. Flowers are then disinfected according to the protocols described herein or by traditional protocols.

Stress-Relieving Treatment

The process of offshoot/flower harvesting, including the transport to the culture facility, is extremely stressful to plant tissue. Physiological changes can be expected. Although it is known in plant tissue culture, that so-called "unspecific shocks" (short heat-, cold-, salt-, dark-, etc.-treatments) can have a positive effect on tissue/cell regeneration, it is evident through experimental results that the "harvesting shock" should be minimized. In some embodiments, a "resting period" of 1, 2, 3, 4, 5, 6, 7, 8, 9, 10 or more days between harvest of the offshoots/flowers and explant extraction may be implemented. In some embodiments, the resting period is implemented in the dark under mild and clean environmental conditions.

Black Barhee date palm Micropropagation Utilizing Offshoot Starting Material
Offshoot Extraction Outer layers of offshoots from a Black Barhee date palm tree are removed gradually, and fibrous tissues are removed until the shoot tip area is exposed. The shoot tip is then excised by cutting a circle around the base of the cylindrical shoot tip at an angle of approximately 45 degrees.

Offshoot Sterilization

In various embodiments, carefully extracted apex-containing core pieces of offshoots ("offshoot samples") are treated for 1-2 or more hours with antioxidant solution. In some embodiments, the offshoot samples are treated for 1, 2, 3, 4, 5, 6, 7, 8, 9, 10 or more hours. In some embodiments, the antioxidant solution includes 50-200 mg/L of ascorbic acid and/or citric acid. In certain embodiments, the antioxidant solution includes 150 mg each per liter of ascorbic acid and citric acid.

In certain embodiments, after treatment with antioxidant solution, the offshoot samples are gas sterilized for 5-240, 10-120, 20-60 or 30-40 minutes. In some embodiments, the offshoot samples are then gas sterilized for 45-120 minutes. In certain embodiments, the duration of gas sterilization is determined based on the offshoot condition (e.g., tissue softness and color etc.). Merely by way of example, in terms of tissue softness, if the tissue is soft, then treatment is for 30-45 minutes. On the other hand, if the tissue is hard then treatment is for 20-60 minutes. In some embodiments, gas sterilization is carried out in a closed container in which chlorine gas is released through the reaction of bleach with concentrated hydrochloric acid. In some embodiments, the container used for gas sterilization is made of a material that may include, but is no way limited to plastic, glass, rubber, composite, and the like. The purpose of the gas sterilization method is that it provides a mild way of penetrating small cavities of the tissue that are not reachable by liquid sterilization due to surface tension.

In some embodiments, after gas sterilization, the offshoot sample is moved into a laminar-flow hood for a 2-40, 4-30 or 6-20 min treatment with sodium hypochloride. In some embodiments, the sodium hypochloride treatment is applied for 12-15 min. In certain embodiments, 0.01%-1.0%, 0.08%-0.8%, 0.1%-0.6%, 0.4%-0.8%, 0.4%-0.6%, 0.5%-0.6% or 0.6%-0.7% sodium hypochloride is applied. In some embodiments, about 0.6% sodium hypochloride is applied for 12-15 minutes.

In some embodiments, the offshoot sample is then washed with 1-6, 2-5 or 3-4 rinses with sterilized reverse osmosis (RO) water. In certain embodiments, after 3 rinses with sterilized RO water, the sterilization procedure is complete.

In certain embodiments, the aforementioned offshoot sterilization protocols are applied to an offshoot of a Black Barhee date palm. In yet additional embodiments, the above-described sterilization methods are believed to be useful for the sterilization of offshoots of other plant types.

Offshoot Culture

In some embodiments, the sterilized core (sterilized as described above or otherwise) is carefully peeled by removal of the leaves until a size of approximately 1.2 cm in diameter and approximately 0.5 cm to 1.5 cm in length (cylinder-like) is reached. In certain embodiments, the cylinder is then cut into pieces longitudinally. In some embodiments, the cylinder is cut into 2-10, 4-9 or 6-8 pieces. In some embodiments, the method produces 1 piece that contain most of the primary apex and additional pieces with secondary apices which may be leaf or flower primordia.

In certain embodiments, the explants are then cultured in groups of 1-6, 2-5 or 3-4, in 10 cm Petri plates (or plates of another convenient size) in the dark at 23-29° C., 24-28° C. or 25-27° C. on an agar-solidified initiation culture medium (e.g. a medium described in Table 4 or Tables 7-11), and subcultured to the same or a different initiation culture medium every 1-8, 3-7 or 4-6 weeks. In some embodiments, the explants are subcultured every 4 weeks. In some embodiments, the initiation medium for one or more subcultures is a medium described in Table 4, or any medium of Tables 7-11. In some embodiments, the initiation medium does not contain 2,4-D. In certain embodiments, the initiation medium contains one or more organics that may include, but are in no way limited to glutamine, adenine, and calcium pantothenate. In certain non-limiting embodiments, the explant is initially cultured in a medium that includes M7, 1/2M7, M20, 1/2M20, M26, M27, M29, 1/2M52, PA01, PA02, PA03, PA04, PA05, PA06, PA07, PAE-1, PAE-1M (this medium is identical to PAE-1, except the concentration of NOA is reduced to 3 mg/L), PAE-9, PAE-71 (this medium is identical to PAE-7, except NAA is omitted and NOA is added at a concentration of 3 mg/L), or PAE-7. In an embodiment, the explant is initially cultured in a medium that includes PAE-1. In an embodiment, the explant is initially cultured in a medium that includes PAE-1M. In an embodiment, the explant is initially cultured in a medium that includes PAE-7. In an embodiment, the explant is initially cultured in a medium that includes PAE-71. In an embodiment, the explant is initially cultured in a medium that includes PAE-9. In some embodiments, the explant is subcultured during the initiation stage in a medium that includes M7, 1/2M7, M20, 1/2M20, M26, M27, M29, 1/2M52, PA01, PA02, PA03, PA04, PA05, PA06, PA07, PAE-1, PAE-1M, PAE-9, PAE-71, or PAE-7. Thus, one or more media may be utilized during the initiation stage. In an embodiment, the explant is subcultured in a medium that includes PAE-1. In an embodiment, the explant is subcultured in a medium that includes PAE-1M. In an embodiment, the explant is subcultured in a medium that includes PAE-7. In an embodiment, the explant is subcultured in a medium that includes PAE-71. In an embodiment, the explant is subcultured in a medium that includes PAE-9. In some embodiments, the explant is initially cultured or subcultured in a medium in which one or more constituents of the above-mentioned media is modified by +0.5-20% (w/v), +2-15% (w/v), or +5-10% (w/v). In some embodiments, the media in which the explant is cultured or subcultured includes charcoal. In some embodiments, explants are subcultured every 1-8 weeks, 3-7 weeks, 4-6 weeks, 4-7 weeks, 5-6 weeks, 6-7 weeks or 5-7 weeks, or more or less frequently, depending upon the condition of the explant. In some embodiments, the above-described initiation protocols are utilized in the furtherance of organogenesis. In some embodiments, the above-described initiation protocols are utilized in the furtherance of embryogenesis. In some embodiments, if organogenesis is desired, then the explants are exposed to light after a period of 4-10 months (preferably 4-6 months). In some embodiments, if embryogenesis is desired, then one or more individual globules are subcultured onto fresh media prior to exposure to light at the end of the 4-10 month period (preferably 4-6 months).

Shoot-Multiplication

In some embodiments, freshly cultured offshoots treated according to the inventive method have a dormancy of 4-10 months during which the explants increase through swelling (water uptake) but rarely display any form of growth. Occasionally, some callus is produced from wounded tissue. In certain embodiments, the cultures are then transferred to light. In some embodiments, the light conditions can be 2000-3000 lux. In some embodiments, light exposure induces organogenesis. In some embodiments, successful initiation is the formation of an organ, or portions thereof (i.e. a shoot or portion thereof), which can be described as initiated material. In some embodiments, initiated material is segregated from the starting explant material and optionally cultured and subcultured during the multiplication stage. In some embodiments, initiation may occur without light stimulation. In some embodiments, the temperature applied at this stage is approximately 25-28° C. In some embodiments, the initial culturing and/or subculturing during the multiplication stage occurs on a medium listed in Table 5 or Tables 7-13. In some embodiments, the initial culturing and/or subculturing during the multiplication stage occurs on a medium listed in Table 12. In some embodiments, the initial culturing and/or subculturing during the multiplication stage occurs on a medium listed in Table 13. In some embodiments, the medium used during the multiplication stage is PAE-21. In some embodiments, the medium used during the multiplication stage is PAE-19. In some embodiments, during the multiplication stage the initiated plant tissue is initially cultured or subcultured in a medium in which one or more constituents of the above-mentioned multiplication media is modified by ±0.5-20% (w/v), ±2-15% (w/v), or ±5-10% (w/v). In some embodiments, the media in which the initiated tissue is cultured or subcultured includes charcoal. In some embodiments, initial culturing and/or subculturing during the multiplication stage occurs on a medium of Table 5 or Tables 7-11 which has been modified by reducing the concentration of one or more hormones to ¾-⅛ of the initial concentration, or ½-⅛ of the initial concentration. In some embodiments, the concentrations of hormones in the media listed in Table 5 or Tables 7-11 are reduced to ⅛ of the initial concentration during the multiplication stage. In some embodiments, initial culturing and/or subculturing during the multiplication stage occurs on a medium of Table 5 or Tables 7-11 which has been modified by reducing the concentration of every constituent except the organics to ¾-⅛ of the initial concentration, or ½-⅛ of the initial concentration. In some embodiments, the concentrations of all constituents except for the organics in the media listed in Table 5 or Tables 7-11 are reduced to ⅛ of the initial concentration during the multiplication stage. In some embodiments, the same medium is utilized during initial culturing and subsequent subculturing. In other embodiments, a different medium is utilized for initial culturing and subsequent subculturing.

In some embodiments, by applying the offshoot culture techniques described herein, after about 2, 3, 4, 5 or 6 months, a single culture (1 culture vessel derived from 1 explant piece) will have produced 10, 20, 30, 40, 50, 60, 70, 80, 90, 100 or more subcultures (~10, 20, 30, 40, 50, 60, 70, 80, 90, 100 or more containers). In some embodiments, production lines are subcultured every 1, 2, 3, 4, 5, 6 or more weeks during the multiplication phase. In some embodiments, production lines are subcultured every 4 weeks. Individual plantlets produced by the production line (usually approximately 6-10 cm in height and greater than about 0.5 cm in stem diameter) are carefully removed and treated for rooting.

Rooting

In certain embodiments, plantlets, approximately 3-15 cm, 5-12 cm or 6-10 cm in height, and approximately 0.2-0.8 cm, 0.3-0.6 cm or 0.4-0.5 cm in stem diameter, are carefully separated from the multiplication cultures for rooting. In some embodiments, the preferred stem diameter is approximately 0.5 cm. Importantly, the rooting techniques described herein often result in almost 100% rooting, which is unusually high.

In some embodiments, the club-shaped terminal of the shoot is identified and carefully cleaned from adhering leaflets and tissue. In certain embodiments, a clean cut is then applied to expose the meristem without damaging it and it is inserted into rooting medium. In some embodiments, the rooting medium includes a rooting medium described in Table 6, or in the examples set forth herein. In some embodiments, the rooting medium is M70 or M82. In some embodiments, the rooting medium includes NAA at a concentration of 0.1 mg/L and sucrose at a concentration of 40-60 g/L. In some embodiments, the concentration of NAA and/or sucrose are modified by approximately up to +20%.

Black Barhee Date Palm Micropropagation Utilizing Flower Starting Material

Flower Sterilization

In certain embodiments, carefully extracted fully closed flower spathes are washed with water and transferred to a laminar-flow hood. In preferred embodiments, the flower spathes are washed in hand-warm water and transferred to the laminar-flow hood. In some embodiments, once the flowers spathes are transferred to the laminar-flow hood, they are wrapped in a bleach-saturated absorbent material and enclosed in an additional layer of material to ensure proper contact with the bleach. In some embodiments, the flower spathes are wrapped in bleach-saturated paper towels and enclosed in aluminum foil to ensure proper contact with the bleach. In some embodiments, the composition of the commercial bleach is approximately 4-6% NaClO by weight. In some embodiments, the duration of bleach treatment ranges from 1-30 minutes, 5-20 minutes or 10-15 minutes. In some embodiments, the duration of treatment is 5 to 15 min, depending on the size of the spathe. Merely by way of example, if the spathe is approximately 10 cm then it may be treated for approximately 5 minutes, whereas if the spathe is approximately 40 cm then it may be treated for approximately 15 minutes or more.

In certain embodiments, after bleach treatment, the spathe is carefully opened with a scalpel and the flower strings are removed with forceps. In some embodiments, including if the flower strings are too long, they are cut into approximately 5 to 10 cm pieces and treated with antioxidant solution (as described above in the protocol for offshoots) for 5-120 minutes, 10-90 minutes, 20-80 minutes or 30-60 minutes. In certain embodiments, once the flower strings are treated with antioxidant solution, they are rinsed with sterilized water to complete the sterilization procedure. Importantly, the sterilization procedures described above can be implemented for male and female flowers alike.

In certain embodiments, the aforementioned flower sterilization protocols are applied to a Black Barhee date palm. In yet additional embodiments, the above-described flower sterilization methods can be implemented for the sterilization of flowers of other plant types.

Flower Culture

In certain embodiments, the sterilized flower strings (regardless of sex) are cut into 0.5-2.5 cm, 0.75-1.75 cm or 1.0-1.5 cm segments, and cultured in groups of 5-30, 10-25 or 15-20 segments in 10 cm Petri plates in the dark at 23-29° C., 24-27° C. or 25-26° C. on agar-solidified initiation culture medium, and subcultured to the same or a different medium every 2-8, 3-7 or 4-6 weeks. In some embodiments, the initiation medium for the flower culture includes one or more media listed in Table 4 or Tables 7-11. In some embodiments, the flower culture includes PAE-9. In some embodiments, the flower culture includes PAE-1M. In some embodiments, the subculturing occurs on the same medium on which the flower string segment was initially placed. In certain embodiments the subculturing occurs on a different medium which includes one or more media listed in Table 4 or Tables 7-11. In some embodiments, the flower subculturing is on a medium that includes PAE-9. In some embodiments, the flower subculturing is on a medium that includes PAE-1M. In some embodiments, the flower subculturing is on a medium that includes PAE-1. In some embodiments, the flower tissue is initially cultured or subcultured in a medium in which one or more constituents of the abovementioned initiation media is modified by ±0.5-20% (w/v), ±2-15% (w/v), or +5-10% (w/v). In some embodiments, the initial initiation medium and/or subculturing medium includes charcoal.

Culture of In Vitro Flowers

When the inventive methods and media described above are implemented, plantlets regenerated in vitro from offshoots can spontaneously produce flowers in vitro. These flowers do not develop in a spathe but rather form a naked single flower or a short naked string of flowers. These flowers, without sterilization or other treatments can be directly cultured again as described in the section above describing flower culture. In certain embodiments, when treated with the inventive media and methods, these cultures react relatively quickly and show a much-reduced dormancy compared to normal.

Flower Multiplication

In various embodiments, flowers freshly cultured utilizing the methods and media described herein have of dormancy of approximately 4-10 months, during which the explants increase through swelling (water uptake) but rarely display any form of growth. Occasionally, when the inventive methods are implemented, some callus is produced from wounded tissue. After the dormancy phase is completed, the explant produces vigorous callus or direct embryos or callus-derived embryos depending on the medium. In certain embodiments, the receptacle is the regenerating flower part. By implementing certain embodiments of the inventive method, about 2 flowers per plate regenerate (from about 50 female or about 150 male flowers per plate). In certain embodiments, the cultures are then transferred to light. Merely by way of example, the light conditions can be 2000-3000 lux. In some embodiments, light is provided in 10-14 hour cycles during the multiplication phase. In some embodiments, light is provided in 12 hour cycles during the multiplication phase. In some embodiments, the temperature for this step is approximately 25-28° C. In some embodiments, by implementing the inventive methods described above, in approximately 2, 3, 4, 5, 6 months or more a single culture (1 culture vessel derived from 1 explant piece) will have produced 10, 20, 30, 40 or more subcultures (10, 20, 30, 40 or more containers). These cultures usually contain a mixture of embryos and shoots. In some embodiments, if the embryo rate is high, subculture production is increased proportionally. In some embodiments, production lines are subcultured every 2-6, 3-5 or 4 weeks during this multiplication stage. Individual plantlets produced by the production line (which are usually about 6-10 cm in height and more than 0.5 cm in stem diameter) are carefully removed and treated for rooting. In some embodiments, initial culturing and/or subculturing during the multiplication stage occurs on a medium of Table 5 or Tables 7-11 which has been modified by reducing the concentration of one or more hormones to ¾-⅛ of the initial concentration, or ½-⅛ of the initial concentration. In some embodiments, the concentrations of one or more hormones in the media listed in Table 5 or Tables 7-11 are reduced to ⅕ of the initial concentration during the multiplication stage. In some embodiments, initial culturing and/or subculturing during the multiplication stage occurs on a medium of Table 5 or Tables 7-11 which has been modified by reducing the concentration of all but the organic constituents to ¾-⅛ of the initial concentration, or ½-⅛ of the initial concentration. In some embodiments, the concentrations of all constituents but the organics in the media listed in Table 5 or Tables 7-11 are reduced to ⅕ of the initial concentration during the multiplication stage. In some embodiments, the same medium is utilized during initial culturing and subsequent subculturing. In other embodiments, a different medium is utilized for initial culturing and subsequent subculturing.

Rooting

In some embodiments, plantlets, 3-15 cm, 5-12 cm or 6-10 cm in height and approximately 0.5 cm in stem diameter are carefully separated from the multiplication cultures described above in this section for rooting. The rooting techniques described herein result in almost 100% rooting, which is unusually high for Black Barhee date palms. In some embodiments, the club-shaped terminal of the shoot is identified and carefully cleaned from adhering leaflets and tissue. In certain embodiments, a clean cut is then applied to expose the meristem without damaging it and it is inserted into rooting medium. In some embodiments, the rooting medium includes a rooting medium described in Table 6, or in the examples set forth herein. In some embodiments, the rooting medium is M70 or M82. In some embodiments, the rooting medium includes NAA at a concentration of 0.1 mg/L and sucrose at a concentration of 40-60 g/L. In some embodiments, the concentration of NAA and/or sucrose are modified by approximately up to +20%.

Indoor Acclimation

In some embodiments, the plantlets are allowed to grow for approximately 3 months under same 10-14 or 12 hour cycle light conditions as above, until approximately 6 inch plants are developed with a substantial number of roots.

Outdoor Acclimation and Establishment

In some embodiments, plants are then transfer to the greenhouse potted into soil. In some embodiments, plants are then planted into the ground after approximately 6-8 months depending on the progress of their growth.

Culture Media

Micropropagated plants are generally grown in vitro in sterile media. The sterile media can be liquid, semi-solid, or solid, and the physical state of the media can be varied by the incorporation of one or more gelling agents. Any gelling agent known in the art that is suitable for use in plant tissue culture media can be used in conjunction with the inventive media. In some embodiments, agar is used for this purpose. Examples of such agars include Agar Type A, E or M and Bacto® Agar. Other exemplary gelling agents include carrageenan, gellan gum (commercially available as Phyta-Gel™, Gelrite® and GelZan™), alginic acid and its salts, and agarose. Blends of these agents, such as two or more of agar, carrageenan, gellan gum, agarose and alginic acid or a salt thereof also can be used. In certain non-limiting examples, the agar utilized is made by Sigma™ Typically, the media used in conjunction with the inventive methods comprises agar with the addition of various compounds such as nutrients, inorganic salts, growth regulators, sugars, vitamins and other compounds. Other media additives can include, but are not limited to, amino acids, macroelements, iron, microelements, inositol and undefined media components such as casein hydrolysates or yeast extracts. For example, the media can include any combination of $NH_4NO_3$; $KNO_3$; $Ca(NO_3)_2$; $K_2SO_4$; $MgSO_4$; $MnSO_4$; $ZnSO_4$; $CuSO_4$; $CaCl_2$; $KI$; $CoCl_2$; $H_3BO_3$; $Na_2MoO_4$; $KH_2PO_4$; $FeSO_4$; $Na_2EDTA$; $Na_2H_2PO_4$; myoinositol; thiamine; pyridoxine; nicotinic acid; glycine; glutamine, adenine, calcium pantothenate, riboflavin; ascorbic acid; silicon standard solution; 3-naphthoxyacetic acid (NAA); indole butyric acid (IBA); 3-in doleacetic acid (IAA); benzylaminopurine (BAP); 6-(gamma-gamma-dimethylallylamino)-purine (2-ip); sugar; agar; carrageenan and charcoal. Non-limiting examples of plant growth regulators include auxins and compounds with auxin-like activity, cytokinins and compounds with cytokinin-like activity. Exemplary auxins include 2,4-dichlorophenoxyacetic acid, IBA, picloram and combinations thereof. Exemplary cytokinins, in addition to meta-topolin and thidiazuron, include adenine hemisulfate, benzyladenine, dimethylallyladenine, kinetin, zeatin and combinations thereof. Gibberellic acid also can be included in the media. One or more sugar can be included in the media and can serve as a carbon source. Non-limiting examples of sugars that may be used include sucrose, glucose, maltose, galactose and sorbitol or combinations thereof.

In various embodiments, including those set forth in Tables 4-9, media described herein are Murashige and Skoog (MS) based. Tables 1-3 indicate the major salts, minor salts, and vitamins and organics of Murashige and Skoog Media, with the exception of sucrose, which is optionally included here in the referenced concentration range of Table 3 or in the other media described in Tables 4-13. The category of organics in MS media may further include indole acetic acid (1-30 mg/l), kinetin (0.04-10 mg/l) and lactalbumin hydrolysate (edamin). For each medium described in Tables 4-9, major salts (macronutrients), minor salts (micronutrients), and organics are included. Concentrations of major salts included in each medium of Tables 4-9 are listed in Table 1, unless medium-specific modifications are indicated (See for example Tables 4-6 and 10-13). Concentrations of minor salts included in each medium of Tables 4-9 are listed in Table 2, unless medium-specific modifications are indicated (See for example Tables 4-6 and 10-13). Concentrations of organics included in each medium of Tables 4-6 are listed in Table 3, unless medium-specific modifications are indicated (See Tables 4-6). In each medium of Tables 4-6, agar is added to a concentration of 6.4±2 g/L, unless medium specific modifications are indicated (See Tables 4-6). In some embodiments, the pH of the media listed in Tables 4-9 or otherwise referenced herein is a pH that is generally hospitable to plants (typically from 4.0-7.0 or 4.5-6.5). In certain embodiments, the pH of the media described herein is adjusted to 5.5-6.3, 5.6-6.2, 5.7-6.1 or 5.8-6.0. In some embodiments, the pH of the media is adjusted to 5.7.

Although relatively narrow concentrations of the cytokinins and auxins are included in the media set forth in Tables 4-13, all of the cytokinins and auxins listed may be present in a range of concentrations.

Merely by way of example NAA, NOA, BAP, 2,4-D, IBA, IAA and 2iP can be present at 0.001 mg/L, 0.01, 0.1, 1, 2, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 mg/L or 0.001 mg/L, 0.01, 0.025, 0.05, 0.075, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.25, 1.50, 1.75, 2.25, 2.5, 2.75, 3.5, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 mg/L.

A pharmaceutically acceptable salt is any salt of the parent compound that is suitable for use in the methods disclosed herein. A pharmaceutically acceptable salt also refers to any salt which may form as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (eg carboxylic acids), one or more protonated basic groups (eg amines), or both (e.g. Zwitterions). Not intended to be limited by the above described compounds, various tautomers of the above compounds may be possible. As used herein, "tautomer" refers to the migration of protons between adjacent single and double bonds. The tautomerization process is reversible. Other tautomers are possible when the compound includes, for example but not limited to, enol, keto, lactamin, amide, imidic acid, amine, and imine groups. Tautomers will generally reach an equilibrium state wherein the double bond is resonantly shared between the two bond lengths.

With the foregoing descriptions in mind, in various embodiments the invention teaches a medium for use in micropropagating a Black Barhee date palm, wherein the medium comprises, consists of, or consists essentially the constituents of any medium of Tables 4-13. In some embodiments, the concentrations of one or more of any of the constituents of Tables 4-13 may be modified by up to approximately +20% of the concentration specifically listed. In some embodiments, the medium is used to micropropagate a Black Barhee date palm. In some embodiments, the medium for use in micropropagating a Black Barhee date palm comprises, consists of, or consists essentially of the constituents of PAE-1, PAE-1M, PAE-9, PAE-71, PAE-21, PAE-19 or PAE-7.

In various embodiments, the invention teaches a method for micropropagating a Black Barhee date palm. In some embodiments, the method includes applying a first medium in vitro to a Black Barhee date palm explant tissue that includes meristematic cells, until a shoot is initiated, wherein the first medium includes: (a) 6-(gamma-gamma-dimethylallylamino)-purine (2-iP), 6-Benzylaminopurine (BAP) and Naphthoxyacetic acid (NOA); or (b) 2,4-Dichlorophenoxyacetic acid (2,4-D), 6-(gamma-gamma-dimethylallylamino)-purine (2-iP) and kinetic (KIN); or (c) 6-Benzylaminopurine (BAP), kinetic (KIN), 1-Naphthaleneacetic acid (NAA). In some embodiments, the method further includes applying a second medium in vitro to the initiated shoot, wherein the second medium includes 6-Benzylaminopurine (BAP). In certain embodiments, the first and/or second media further includes charcoal. In some embodiments, the first medium includes 6-(gamma-gamma-dimethylallylamino)-purine (2-iP), 6-Benzylaminopurine (BAP) and Naphthoxyacetic acid (NOA). In some embodiments, the first medium includes 2-iP at a concentration of 1-3 mg/L, BAP at a concentration of 0.5-1.5 mg/L, and NOA at a concentration of 2.0-6.5 mg/L. In an embodiment, the first medium includes 2-iP at a concentration of 2 mg/L, BAP at a concentration of 1 mg/L, and NOA at a concentration of 5 mg/L. In another embodiment, the first medium includes 2-iP at a concentration of 2 mg/L, BAP at a concentration of 1 mg/L, and NOA at a concentration of 3 mg/L. In other embodiments, the first medium includes 2,4-Dichlorophenoxyacetic acid (2,4-D), 6-(gamma-gamma-dimethylallylamino)-purine (2-iP) and kinetic (KIN). In some embodiments, the first medium includes 2,4-D at a concentration of 0.5-1.5 mg/L, 2-iP at a concentration of 2-4 mg/L, and KIN at a concentration of 2-4 mg/L. In an embodiment, the first medium includes 2,4-D at a concentration of 1 mg/L, 2-iP at a concentration of 3 mg/L, and KIN at a concentration of 3 mg/L. In yet other embodiments, the first medium includes 6-Benzylaminopurine (BAP), kinetic (KIN), and 1-Naphthaleneacetic acid (NAA). In some embodiments, the first medium includes 6-Benzylaminopurine (BAP) at a concentration of 0.05-0.15 mg/L, kinetic (KIN) at a concentration of 0.005-0.015 mg/L, and 1-Naphthaleneacetic acid (NAA) at a concentration of 0.5-1.5 mg/L. In an embodiment, the first medium includes 6-Benzylaminopurine (BAP) at a concentration of 0.1 mg/L, kinetic (KIN) at a concentration of 0.1 mg/L, and 1-Naphthaleneacetic acid (NAA) at a concentration of 1 mg/L. In additional embodiments, the first medium includes BAP at a concentration of 0.05-0.15 mg/L, KIN at a concentration of 0.005-0.015 mg/L, and 2-Naphthoxyacetic acid (NOA) at a concentration of 2-4 mg/L. In an embodiment, the first medium includes BAP at a concentration of 0.1 mg/L, KIN at a concentration of 0.01 mg/L, and 2-Naphthoxyacetic acid (NOA) at a concentration of 3 mg/L. In certain embodiments, the first medium further includes any of about 25%, about 50%, about 75%, about 90% or 100% of Murashige and Skoog standard concentrations of major salts and/or minor salts and/or organics. In some embodiments, the concentration of Murashige and Skoog standard concentrations of major salts and/or minor salts and/or organics is 20-100%, 30-90%, 40-80%, or 50-70%. In certain embodiments, the concentrations of major salts and/or minor salts and/or organics in the first medium are according to the concentrations of those constituents listed in Table 10 for PAE-1, PAE-9, or PAE-7. In some embodiments the concentrations of major salts and/or minor salts and/or organics of the first medium are within +20% of the concentrations of those constituents listed in Table 10 for PAE-1, PAE-9, or PAE-7. In certain embodiments, the first medium comprises, consists of, or consists essentially of the components of PAE-1, PAE-1M, PAE-9, PAE-7, or PAE-71. In some embodiments, the second medium includes BAP at a concentration of 0.5-1.5 mg/L. In some embodiments, the second medium includes BAP at a concentration of 1 mg/L. In certain embodiments, the second medium further includes any of about 25%, about 50%, about 75%, about 90% or 100% of Murashige and Skoog standard concentrations of major salts and/or minor salts and/or organics. In some embodiments, the concentration of Murashige and Skoog standard concentrations of major salts and/or minor salts and/or organics is 20-100%, 30-90%, 40-80%, or 50-70%. In certain embodiments, the concentrations of major salts and/or minor salts and/or organics in the second medium are according to the concentrations of those constituents listed in Table 12 for PAE-19 or PAE-21. In some embodiments the concentrations of major salts and/or minor salts and/or organics of the second medium are within +20% of the concentrations of those constituents listed in Table 12 for PAE-19 or PAE-21. In certain embodiments, the second medium comprises, consists of, or consists essentially of the components of PAE-19 or PAE-21 listed in Table 12. In some embodiments, the second medium comprises, consists of, or consists essentially of the components of PAE-21. In some embodiments, the second medium comprises, consists of, or consists essentially of PAE-19. In some embodiments, after initiation and multiplication are accomplished, the tissue is subject to rooting (and optionally elongation prior to rooting). In some embodiments, rooting is accomplished by exposing/incubating the multiplied tissue to any rooting medium described herein.

In various embodiments, the invention teaches a method for micropropagating a Black Barhee date palm. In some embodiments, the method includes applying a medium in vitro to an initiated Black Barhee date palm shoot derived from an explant, wherein the medium includes 6-Benzylaminopurine (BAP). In some embodiments, the medium includes BAP at a concentration of 0.5-1.5 mg/L. In some embodiments, the medium includes BAP at a concentration of 1 mg/L. In certain embodiments, the medium further includes any of about 25%, about 50%, about 75%, about 90% or 100% of Murashige and Skoog standard concentrations of major salts and/or minor salts and/or organics. In some embodiments, the concentration of Murashige and Skoog standard concentrations of major salts and/or minor salts and/or organics is 20-100%, 30-90%, 40-80%, or 50-70%. In certain embodiments, the concentrations of major salts and/or minor salts and/or organics in the medium are according to the concentrations of those constituents listed in Table 12 for PAE-19 or PAE-21. In some embodiments the concentrations of major salts and/or minor salts and/or organics of the medium are within +20% of the concentrations of those constituents listed in Table 12 for PAE-19 or PAE-21. In certain embodiments, the medium comprises, consists of, or consists essentially of the components of PAE-19 or PAE-21 listed in Table 12. In some embodiments, the medium comprises, consists of, or consists essentially of the components of PAE-21. In some embodiments, the medium comprises, consists of, or consists essentially of the components of PAE-19.

In various embodiments, the date palm explant tissue in the methods described above is from a male Black Barhee date palm. In some embodiments, the Black Barhee date palm explant tissue in the methods described above is from a female Black Barhee date palm.

In various embodiments, the Black Barhee date palm explant in the methods described above includes plant tissue from an offshoot of a Black Barhee date palm. In some embodiments, the Black Barhee date palm explant includes plant tissue from a flower, a leaf, or a bud of a Black Barhee date palm. In some embodiments, the explant tissue, whether from an offshoot, a flower, a leaf, or a bud, comprises meristematic cells.

In various embodiments, the invention teaches a method for micropropagating a Black Barhee date palm. In some embodiments, the method includes initiating a shoot in vitro from a Black Barhee date palm explant on a first medium, and multiplying (i.e. growing, because now an additional shoot is being produced) the shoot initiated from the explant in vitro on a second medium. In some embodiments, the first medium comprises, consists of, or consists essentially of the constituents of M7, 1/2M7, M20, 1/2M20, M26, M27, M28, M29, M52, 1/2M52, M53, M63, PAE-1, PAE1-M, PAE-9, PAE-7, PAE-71, or any medium of Tables 7-13. In some embodiments, the second medium comprises, consists of, or consists essentially of the constituents of M7, M36, PAE-21, PAE-19, or any medium of Tables 7-13, or any medium of Tables 7-13 in which the concentration of hormones has been reduced to ¾ to ⅛ of the initial concentration listed in the table, or ½ to ⅛ of the initial concentration listed in the table. In some embodiments, the concentrations of hormones in any medium listed in Table 5 or Tables 7-13 are reduced to ⅕ of the initial concentration listed in the table during the multiplication stage. In some embodiments, the second medium comprises, consists of, or consists essentially of the constituents of M7, M36, any medium of Tables 7-13, or any medium of Tables 7-13 in which the concentrations of all constituents except the organics has been reduced to ¾ to ⅛ of the initial concentration listed in the table, or ½ to ⅛ of the initial concentration listed in the table. In some embodiments, the concentrations of all constituents except the organics in any medium listed in Table 5 or Tables 7-13 are reduced to ⅕ of the initial concentration listed in the table for the multiplication stage. In certain embodiments, the date palm explant includes plant tissue from an offshoot of a date palm. In certain embodiments the date palm explant includes plant tissue from a flower of a date palm. In some embodiments, the plant tissue is obtained by any means described herein. In certain embodiments, the plant tissue is treated with an antioxidant solution and/or sterilized by any method described herein.

In some embodiments, the method further includes transferring one or more of the multiplied shoots (i.e. a grown shoot that is large enough to be isolated and established on a rooting medium described herein) to a rooting medium that comprises, consists of, or consists essentially of the constituents of a medium of Table 6. In some embodiments, the rooting medium is any rooting medium described herein.

In certain embodiments, the invention teaches a method for micropropagating a Black Barhee date palm by utilizing one or more media comprising, consisting of, or consisting essentially of the constituents of a medium of Tables 4 or 7-13 during the initiation stage (as described herein). In some embodiments, the invention teaches a method for micropropagating a Black Barhee date palm by utilizing one or more media comprising, consisting of, or consisting essentially of the constituents of a medium of Table 5, Tables 7-13, or modified versions of any medium of Tables 7-9 in which the concentrations of one or more hormones and/or other constituents have been reduced as described above for the multiplication stage (as described herein). In certain embodiments, the invention teaches a method for micropropagating a Black Barhee date palm by utilizing one or more media comprising, consisting of or consisting essentially of the constituents of a medium of Table 6 for the rooting stage (as described herein). In some embodiments one or more media utilized for the rooting stage comprises, consists of, or consists essentially of the constituents of any medium described herein as a rooting medium. In some embodiments, the invention teaches utilizing one or more media comprising, consisting of or consisting essentially of the constituents of one or more media of Tables 4 or 7-13 for the initiation stage and/or one or more media comprising, consisting of, or consisting essentially of the constituents of one or more media of Table 5, Table 7-13, or modified versions of any medium of Tables 7-13 in which the concentrations of hormones and/or other constituents have been reduced as described above for the multiplication stage and/or one or more medium comprising, consisting of, or consisting essentially of the constituents of one or more media of Table 6 or any other medium described herein for the rooting stage.

In some embodiments, the invention teaches a kit that includes one or more media comprising, consisting of, or consisting essentially of the constituents of one or more media described in any of Tables 4-13. In some embodiments, the kit includes one or more media comprising, consisting of, or consisting essentially of the constituents of one or more media described in Tables 4-13 and/or one or more media comprising, consisting of, or consisting essentially of the constituents of one or more media described in Table 5 or a low (reduced) hormone and/or other constituents version of any medium described in tables 4-13 (as described above) and/or one or more media comprising, consisting of, or consisting essentially of the constituents of one or more media described in Table 6 or any rooting medium described herein.

In some embodiments, the kit further includes a tissue sample from any source described herein, obtained by any method described herein, and optionally treated with any antioxidant solution described herein and/or sterilized by any method described herein. In some embodiments the tissue sample includes meristematic cells of a Black Barhee date palm.

In certain embodiments, the kit includes one or more containers configured for performing one or more stages of the tissue culturing process described herein (i.e. initiation, multiplication, or rooting). Non-limiting examples of tissue culture dishes are depicted in the drawings of the present application.

In some embodiments, the kit includes one or more containers for sterile storage of one or more media and/or tissue sample and/or explant described herein. In certain embodiments, the different components of the one or more media can be packaged in separate containers and mixed before use. In certain embodiments, one or more media can be provided pre-mixed and optionally marked with an expiration date for convenient storage and use.

In some embodiments, the kit further includes instructional materials for utilizing all or a portion of the contents contained therein. In some embodiments, the instructional materials may be printed on paper or other substrate, and/or may be supplied as an electronic-readable media, such as a floppy disc, CD-ROM, DVD-ROM, Zip disc, videotape, audiotape, etc. Detailed instructions may not be physically associated with the kit; instead, a user may be directed to an internet web site specified by the manufacturer or distributor of the kit, or supplied by electronic mail.

In some embodiments, the concentrations of one or more constituents of the media described herein above and below, and utilized in conjunction with the media/compositions, methods and kits described herein are consistent with those listed in the referenced tables. In other embodiments, the concentrations of one or more constituents of the media described herein above and below and utilized in conjunction with the inventive media/compositions, methods and kits are up to approximately +20% of the values stated in the tables.

In some embodiments, the invention teaches a Black Barhee date palm plant, a Black Barhee date palm tissue, or a Black Barhee date palm cell resulting from the process of micropropagation, or a stage within the process of micropropagation, according to one or more method described herein and/or by utilizing one or more medium described herein during one or more stage of micropropagation. The inventive plant, plant tissue, or plant cell is intended to include a plant, plant tissue or plant cell at any stage of development after any stage of the process of micropropagation described herein has started. Thus, for example, a plant, a plant tissue, or a plant cell that results from initiation, multiplication, rooting, acclimation, or that has been temporarily or permanently planted in soil, after one or more of the protocols described herein (or one or more portions thereof) has been applied, is within the scope of the present invention. Furthermore, a plant, plant tissue, or plant cell that results after exposing starting material of a Black Barhee date palm to any one or more medium that includes the constituents of any one or more medium described herein, is within the scope of the present invention. In some embodiments, the starting material includes all or a portion of a flower of a Black Barhee date palm. In some embodiments, the starting material includes all or a portion of a bud of a Black Barhee date palm. In some embodiments, the starting material includes a portion of an offshoot of a Black Barhee date palm. In some embodiments, the starting material includes a cell of a Black Barhee date palm.

In some embodiments, the invention teaches a Black Barhee date palm plant resulting after exposing a tissue or a cell of a Black Barhee date palm to media comprising, consisting of, or consisting essentially of the constituents of a medium selected from PAE-1, PAE-1M, PAE-9, PAE-71, PAE-19, PAE-21 and PAE-7. In some embodiments, one or more of the constituents of the aforementioned media to which the tissue or a cell of a Black Barhee date palm has been exposed is varied by +20%. In certain embodiments, the origin of the tissue is an offshoot, a flower, a leaf, or a bud.

In some embodiments, the invention teaches a Black Barhee date palm plant cell resulting from exposing a tissue or a cell of a Black Barhee date palm (e.g. as described herein) to media comprising, consisting of, or consisting essentially of the constituents of a medium selected from the group consisting of PAE-1, PAE-1M, PAE-9, PAE-21, PAE-71 and PAE-7. In some embodiments, one or more of the constituents of the aforementioned media to which the tissue or a cell of a Black Barhee date palm has been exposed is varied by +20%.

In some embodiments, the inventive tissue or cell originates from a callus formed on an explant of a Black Barhee date palm treated with one or more media types described herein. In some embodiments, the explant includes tissue from a flower, a bud, a leaf, or an offshoot of a Black Barhee date palm.

In various embodiments, the invention teaches a Black Barhee date palm plant resulting from exposing a globule of a callus of a Black Barhee date palm explant to a medium comprising, consisting of, or consisting essentially of the constituents of a medium selected from PAE-1, PAE-1M, PAE-9, PAE-19, PAE-21, PAE-71 and PAE-7, wherein a starting material from which the callus is formed is a flower, a bud, a leaf, or an offshoot of a Black Barhee date palm. In some embodiments, one or more of the constituents of the aforementioned media to which the globule of a callus of the Black Barhee date palm explant has been exposed is varied by +20%.

In some embodiments, the present invention teaches a method for generating revenue for a person or an entity (corporation, company, and the like) by selling one or more micropropagated plant, a plant tissue, or a plant cell, at any stage described herein, resulting from any one or more method described herein and/or by using any one or more medium described herein. In some embodiments, the invention teaches selling a plant that has been micropropagated according to one or more methods described herein. In some embodiments, the method teaches selling a portion of a plant, a cell of a plant, or group of cells of a plant. In some embodiments, the plant, plant cell, or plant tissue is of Black Barhee date palm that has been micropropagated according to any method described herein, or that is at any stage of the micropropagation process described herein, and/or that has been treated with (i.e. exposed to) any of one or more medium described herein.

EXAMPLES

Example 1

Micropropagation of a Black Barhee Date Palm Organogenesis

Selected offshoots of a Black Barhee date palm are 3-6 years old with an average weight of 3-10 kg. Before removing the offshoots, the connection between the offshoots and mother plant is established. Shoot tips and buds are obtained as described above. Alternatively, flowers may be prepared as described above.

Antioxidant Treatment

Shoot tips or flower tissue is transferred to an antioxidant solution containing 100 mg of ascorbic acid and 150 mg of citric acid to avoid phenolic oxidation.

Incubation

Disinfected shoot tips and buds or flowers are transferred to an incubation media selected from one or more of PA01, PA02, PA03, PA04, PA05, PA06, PA07, PAE-1, PAE-1M, PAE-7, PAE-71, and PAE-9, as described in Table 9. These explants are then incubated for 4-6 months, and subcultured in fresh media approximately every month. After 4-6 months of incubation, the transplants are transferred to light with a photoperiod of 16 h at 25° C. Optionally, PAE-9 can be used for the initiation stage of an explant derived from flower starting material, whereas PAE-1M can be used for the initiation stage of an explant derived from shoot starting material ("shoot tip" starting material).

Shoot Multiplication

For the multiplication stage, ⅕ concentration of all constituents (except Nicotinic acid, Thiamine HCl, Pyridoxine HCl, Glycine, Glutamine, Adenine, Ca-pantothenate, and myoinositol) of any of PA01, PA02, PA03, PA04, PA05, PA06 and PA07 can be used (applied to initiated material). Alternatively, for multiplication, PAE-21 or PAE-19 can be used (applied to initiated material).

Shoot Elongation

Multiplied shoots are transferred to a MS media containing NAA 1 mg/L, BA 0.5 mg/L, Kinetin 0.5 mg/L and IBA 0.5 mg/L.

Rooting

Elongated shoots are rooted in a medium containing NAA 0.1 mg/L in the presence of 40-60 g/L of sucrose.

Media Tables

TABLE 1

Major Salts (Macronutrients)

| Component | mg/L |
| --- | --- |
| Ammonium nitrate ($NH_4NO_3$) | 1,650 ± 2 |
| Calcium chloride ($CaCl_2$ $2H_2O$) | 440 ± 2 |

TABLE 1-continued

Major Salts (Macronutrients)

| Component | mg/L |
| --- | --- |
| Magnesium sulphate ($MgSO_4$ $7H_2O$) | 370 ± 2 |
| Potassium phosphate ($KH_2PO_4$) | 170 ± 2 |
| Potassium nitrate ($KNO_3$) | 1,900 ± 2 |

TABLE 2

Minor Salts (Micronutrients)

| Component | mg/L |
| --- | --- |
| Boric acid ($H_3BO_3$) | 6.2 ± 0.2 |
| Cobalt chloride ($CoCl_2$ $6H_2O$) | 0.025 ± .002 |
| Cupric sulphate ($CuSO_4$ $5H_2O$) | 0.025 ± .002 |
| Ferrous sulphate ($FeSO_4$ $7H_2O$) | 27.8 ± 0.2 |
| Manganese sulphate ($MnSO_4$ $4H_2O$) | 22.3 ± 2 |
| Potassium iodide (KI) | 0.83 ± .02 |
| Sodium molybdate ($Na_2MoO_4$ $2H_2O$) | 0.25 ± .02 |
| Zinc sulphate ($ZnSO_4 \cdot 7H_2O$) | 8.6 ± 0.2 |
| Ethylenediaminetetraacetic acid ($Na_2EDTA$ $2H_2O$) | 37.2 ± 2 |

TABLE 3

Organics

| Component | mg/L (unless otherwise noted) |
| --- | --- |
| Myo-Inositol | 100 ± 2 |
| Thiamine | 0.4 ± 0.3 |
| Pyridoxine | 0.5 ± 0.2 |
| Nicotinic acid | 0.5 ± 0.2 |
| Glycine | 2 ± 0.5 |
| Sucrose | 30 g/L ± 2 |

TABLE 4

Initiation Media I

| Medium Name | Modification to MS Salts (If not modified from concentrations in Tables 1 & 2 "NA") | Modification(s) to Organics (Hormones, Vitamins, Sugars, Agar, etc.) |
| --- | --- | --- |
| M7 | NA | 1. BAP = 1 ± 0.2 mg/L<br>2. Charcoal = 500 ± 50 mg/L |
| 1/2M7 | 50% MS Salts | 1. BAP = 1 ± 0.2 mg/L<br>2. Charcoal = 500 ± 50 mg/L |
| M20 | NA | 1. BAP = 3 ± 0.2 mg/L<br>2. NAA = 1 ± 0.2 mg/L<br>3. Charcoal = 500 ± 50 mg/L |
| 1/2M20 | 50% MS Salts | 1. BAP = 3 ± 0.2 mg/L<br>2. NAA = 1 ± 0.2 mg/L<br>3. Charcoal = 500 ± 50 mg/L |
| M26 | NA | 1. $NaH_2PO_4$ = 170 ± 10 mg/L<br>2. Glutamine = 200 ± 10 mg/L<br>3. BAP = 1 ± 0.2 mg/L<br>4. 2iP = 2 ± 0.2 mg/L<br>5. NAA = 1 ± 0.2 mg/L<br>6. NOA = 1 ± 0.2 mg/L<br>7. Ascorbic acid = 50 ± 5 mg/L<br>8. Charcoal = 500 ± 50 mg/L |
| M27 | NA | 1. $NaH_2PO_4$ = 170 ± 10 mg/L<br>2. Glutamine = 200 ± 10 mg/L<br>3. BAP = 5 ± 0.2 mg/L<br>4. 2iP = 1 ± 0.2 mg/L<br>5. NAA = 0.1 mg/L<br>6. NOA = 0.5 ± 0.2 mg/L |

TABLE 4-continued

Initiation Media I

| Medium Name | Modification to MS Salts (If not modified from concentrations in Tables 1 & 2 "NA") | Modification(s) to Organics (Hormones, Vitamins, Sugars, Agar, etc.) |
|---|---|---|
| | | 7. Ascorbic acid = 50 ± 5 mg/L |
| | | 8. Charcoal = 500 ± 50 mg/L |
| M28 | NA | 1. $NaH_2PO_4$ = 170 ± 10 mg/L |
| | | 2. Glutamine = 200 ± 10 mg/L |
| | | 3. BAP = 1 ± 0.2 mg/L |
| | | 4. 2iP = 1 ± 0.2 mg/L |
| | | 5. Kinetin = 1 ± 0.2 mg/L |
| | | 6. NOA = 0.5 ± 0.2 mg/L |
| | | 7. Ascorbic acid = 50 ± 5 mg/L |
| | | 8. Charcoal = 500 ± 50 mg/L |
| M29 | NA | 1. $NaH_2PO_4$ = 170 ± 10 mg/L |
| | | 2. Glutamine = 200 ± 10 mg/L |
| | | 3. BAP = 1 ± 0.2 mg/L |
| | | 4. 2iP = 2 ± 0.2 mg/L |
| | | 5. NOA = 0.5 ± 0.2 mg/L |
| | | 6. Ascorbic acid = 50 ± 5 mg/L |
| | | 7. Charcoal = 500 ± 50 mg/L |
| M52 | NA | 1. $NaH_2PO_4$ = 170 ± 10 mg/L |
| | | 2. Thiamine HCl = 5 ± 1 mg/L |
| | | 3. Nicotinic acid = 5 ± 1 mg/L |
| | | 4. Pyridoxine HCl = 2.5 ± .5 mg/L |
| | | 5. Ca-pantothenate = 2.5 ± .5 mg/L |
| | | 6. Inositol = 10 ± 1 mg/L |
| | | 7. Glycine = 3 ± .2 mg/L |
| | | 8. Glutamine = 20 ± 2 mg/L |
| | | 9. NAA = 5 ± 1 mg/L |
| | | 10. NOA = 5 ± 1 mg/L |
| | | 11. BAP = 1 ± .1 mg/L |
| | | 12. Kinetin = 1 ± .1 mg/L |
| | | 13. 2iP = 1 ± .1 mg/L |
| | | 14. Citric acid = 75 ± 5 mg/L |
| | | 15. Ascorbic acid = 75 ± 5 mg/L |
| | | 16. Charcoal = 1.5 g/L |
| | | 17. Agar (Gelrite) = 1.3 g/L |
| | | 18. pH = 5.6 ± .1 |
| 1/2M52 | 50% MS salts | 1. $NaH_2PO_4$ = 170 ± 10 mg/L |
| | | 2. Thiamine HCl = 5 ± 1 mg/L |
| | | 3. Nicotinic acid = 5 ± 1 mg/L |
| | | 4. Pyridoxine HCl = 2.5 ± .5 mg/L |
| | | 5. Ca-pantothenate = 2.5 ± .5 mg/L |
| | | 6. Inositol = 10 ± 1 mg/L |
| | | 7. Glycine = 3 ± .2 mg/L |
| | | 8. Glutamine = 20 ± 2 mg/L |
| | | 9. NAA = 5 ± 1 mg/L |
| | | 10. NOA = 5 ± 1 mg/L |
| | | 11. BAP = 1 ± .1 mg/L |
| | | 12. Kinetin = 1 ± .1 mg/L |
| | | 13. 2iP = 1 ± .1 mg/L |
| | | 14. Citric acid = 75 ± 5 mg/L |
| | | 15. Ascorbic acid = 75 ± 5 mg/L |
| | | 16. Charcoal = 1.5 g/L |
| | | 17. Agar (Gelrite) = 1.3 g/L, pH = 5.6 ± .1 |
| M53 | NA | 1. $NaH_2PO_4$ = 10 ± 1 mg/L |
| | | 2. Thiamine HCl = 5 ± 1 mg/L |
| | | 3. Nicotinic acid = 5 ± 1 mg/L |
| | | 4. Pyridoxine HCl = 2.5 ± .5 mg/L |
| | | 5. Ca-pantothenate = 2.5 ± .5 mg/L |
| | | 6. Inositol = 10 ± 1 mg/L |
| | | 7. Glycine = 3 ± .2 mg/L |
| | | 8. Glutamine = 20 ± 2 mg/L |
| | | 9. 2,4-D = 1 ± .1 mg/L |
| | | 10. Kinetin = 3 ± .1 mg/L |
| | | 11. 2iP = 3 ± .1 mg/L |
| | | 12. Citric Acid = 75 ± 5 mg/L |
| | | 13. Ascorbic Acid = 75 ± 5 mg/L |
| | | 14. Charcoal = 500 ± 50 mg/L |
| M63 | NA | 1. Nicotinic Acid = 0.5 ± .1 mg/L |
| | | 2. Pyridoxine HCl = 0.5 ± .1 mg/L |
| | | 3. Thiamine = 0.5 ± .1 mg/L |
| | | 4. Glycine = 2 ± .1 mg/L |
| | | 5. Inositol = 10 ± 1 mg/L |
| | | 6. Glutamine = 10 ± 1 mg/L |
| | | 7. Adenine = 30 ± 2 mg/L |
| | | 8. 2,4-D = 1 ± .1 mg/L |
| | | 9. Charcoal = 500 ± 50 mg/L |

TABLE 5

Multiplication Media I

| Medium Name | Modification(s) to MS Salts (if not modified from concentrations in Tables 1&2 "NA") | Modification(s) to Organics (Hormones, Vitamins, Sugars, Agar, etc.) |
|---|---|---|
| M7 | NA | 1. BAP = 1 ± 0.2 mg/L |
| | | 2. Charcoal = 500 ± 50 mg/L |
| M36 | NA | 1. $NaH_2PO_4$ = 150 ± 10 mg/L |
| | | 2. Glutamine = 200 ± 10 mg/L |
| | | 3. BAP = 2 ± 0.2 mg/L |
| | | 4. 2iP = 4 ± 0.2 mg/L |
| | | 5. NAA = 1 ± 0.2 mg/L |
| | | 6. NOA = 1 ± 0.2 mg/L |
| | | 7. Charcoal = 500 ± 50 mg/L |

TABLE 6

Rooting Media

| Medium Name | Modification(s) to MS Salts (if not modified from concentrations in Tables 1&2 "NA") | Modification(s) to Organics (Hormones, Vitamins, Sugars, Agar, etc.) |
|---|---|---|
| M70 | NA | 1. NAA = 1 ± 0.2 mg/L |
| | | 2. Agar (Gelrite) = 1.5 ± 0.2 g/L |
| M82 | NA | 1. NAA = 0.1 ± .02 mg/L |
| | | 2. Charcoal = 500 ± 50 mg/L |

For each type of medium listed in Tables 7-9, the amount of each component may be adjusted by up to +20%, with the volume of water adjusted appropriately such that the total volume of for each medium prepared is 1 L. One of skill in the art would understand that the recipe for each medium type can be adjusted appropriately if a total volume of less or more than 1 L is desired for any particular application. For each table herein, "BTV 1 L" means that a quantity of water is added to the medium recipe such that the total volume of the medium is 1 L.

For each medium listed in Tables 7-9 each of the major salts of Table 1 and minor salts of Table 2 are added according to the concentrations listed in Table 1 and Table 2. In addition, for each medium listed in Tables 7-9 each of the organics listed in Table 3 are added according to the concentrations listed in Table 3. Any additional major salts, minor salts, and organics that are included in the media of Tables 7-9 are specifically listed in those tables with appropriate concentrations or ranges of concentrations noted.

TABLE 7

Initiation Media II

| | Medium Type | | | | | | | |
|---|---|---|---|---|---|---|---|---|
| | PAEX1 | PAEX2 | PAEX3 | PAEX4 | PAEX5 | PAEX6 | PAEX7 | PAEX8 |
| DI Water (ml/L) | BTV 1 L | BTV 1 L | BTV 1 L | BTV 1 L | BTV 1 L | BTV 1 L | BTV 1 L | BTV 1 L |
| Glutamine (mg/L) | 10 | 10 | 10 | 10 | 10 | 10 | 10 | 10 |
| Ca-Pantothenate (mg/L) | 2.5 | 2.5 | 2.5 | 2.5 | 2.5 | 2.5 | 2.5 | 2.5 |
| Adenine (mg/L) | 3 | 3 | 3 | 3 | 3 | 3 | 3 | 3 |
| Ascorbic Acid (mg/L) | 75 | 75 | 75 | 75 | 75 | 75 | 75 | 75 |
| BAP (mg/L) | | | | 1 | 5 | 3 | | 5 |
| IAA (mg/L) | | | | | | | | |
| Kinetin (mg/L) | | | | | | | | |
| NOA (mg/L) | | | | | | | | |
| NAA (mg/L) | | | | | | | | |
| 2,4 D (mg/L) | | 1 | 5 | | | | | |
| 2iP (mg/L) | | | | | | 3 | 3 | 3 |
| Activated charcoal (g/L) | 0.5 | 0.5 | 0.5 | 0.5 | 0.5 | 0.5 | 0.5 | 0.5 |
| Agar (g/L) | 6.6 | 6.6 | 6.6 | 6.6 | 6.6 | 6.6 | 6.6 | 6.6 |

TABLE 8

Initiation Media III

| | Medium Type | | | | | | |
|---|---|---|---|---|---|---|---|
| | PAEX9 | PAEX10 | PAEX11 | PAEX12 | PAEX13 | PAEX14 | PAEX15 |
| DI Water (ml/L) | BTV 1 L | BTV 1 L | BTV 1 L | BTV 1 L | BTV 1 L | BTV 1 L | BTV 1 L |
| Glutamine (mg/L) | 10 | 10 | 10 | 10 | 10 | 10 | 10 |
| Ca-Pantothenate (mg/L) | 2.5 | 2.5 | 2.5 | 2.5 | 2.5 | 2.5 | 2.5 |
| Adenine (mg/L) | 3 | 3 | 3 | 3 | 3 | 3 | 3 |
| Ascorbic Acid (mg/L) | 75 | 75 | 75 | 75 | 75 | 75 | 75 |
| BAP (mg/L) | 5 | 5 | 5 | 5 | | | |
| IAA (mg/L) | | | | | | 1 | 1 |
| Kinetin (mg/L) | 3 | 3 | 3 | 3 | | | |
| NOA (mg/L) | | 5 | 5 | 5 | | | |
| NAA (mg/L) | | | | | 1 | | 1 |
| 2,4 D (mg/L) | | | 1 | 5 | | | |
| 2iP (mg/L) | 3 | 3 | 3 | 3 | | | |
| Activated charcoal (g/L) | 0.5 | 0.5 | 0.5 | 0.5 | 0.5 | 0.5 | 0.5 |
| Agar (g/L) | 6.6 | 6.6 | 6.6 | 6.6 | 6.6 | 6.6 | 6.6 |

TABLE 9

Initiation Media IV

| | Medium Type | | | | | | |
|---|---|---|---|---|---|---|---|
| | PA01 | PA02 | PA03 | PA04 | PA05 | PA06 | PA07 |
| DI Water (ml/L) | BTV 1 L | BTV 1 L | BTV 1 L | BTV 1 L | BTV 1 L | BTV 1 L | BTV1 L |
| Glutamine (mg/L) | 10 | 10 | 10 | 10 | 10 | 10 | 10 |
| Ca-Pantothenate (mg/L) | 2.5 | 2.5 | 2.5 | 2.5 | 2.5 | 2.5 | 2.5 |
| Adenine (mg/L) | 3 | 3 | 3 | 3 | 3 | 3 | 3 |
| Ascorbic Acid (mg/L) | 75 | 75 | 75 | 75 | 75 | 75 | 75 |
| IBA (mg/L) | | | | | 0.2 | | |
| BAP (mg/L) | | | | | 1 | | 1 |
| IAA (mg/L) | 0.5 | 1 | | | | | 1 |
| Kinetin (mg/L) | | | 1 | | | | |
| NOA (mg/L) | | 1 | 1 | | | 3 | |
| NAA (mg/L) | 0.5 | 1 | 1 | 0.1 | | 1 | 0.5 |
| 2,4 D (mg/L) | | | | | | | |
| 2iP (mg/L) | 0.2 | 0.2 | 2 | 2 | | 0.5 | 1 |
| Activated charcoal (g/L) | 0.5 | 0.5 | 0.5 | 0.5 | 0.5 | 0.5 | 0.5 |
| Agar (g/L) | 6.6 | 6.6 | 6.6 | 6.6 | 6.6 | 6.6 | 6.6 |

TABLE 10

| Initiation Media V | | | | |
|---|---|---|---|---|
| Media - Components | Unit | PAE-1 | PAE-9 | PAE-7 |
| Distilled Water | mL | 990.0 | 990.0 | 990.0 |
| Sucrose | g/L | 30.0 | 30.0 | 30.0 |
| Ammonium Nitrate ($NH_4NO_3$) | mg/L | 825.0 | 825.0 | 825.0 |
| Boric Acid ($H_3BO_3$) | mg/L | 3.10 | 3.10 | 3.10 |
| Calcium Chloride, Anhydrous ($CaCl_2$) | mg/L | 166.050 | 166.050 | 166.050 |
| Cobalt Chloride, Hexahydrate ($CoCl_2 \cdot 6H_2O$) | mg/L | 0.0125 | 0.0125 | 0.0125 |
| Cupric Sulfate, Pentahydrate ($CuSO_4 \cdot 5H_2O$) | mg/L | 0.0125 | 0.0125 | 0.0125 |
| EDTA, Disodium, Dihydrate ($C_{10}H_{14}N_2Na_2O_8 \cdot 2H_2O$) | mg/L | 18.630 | 18.630 | 18.630 |
| Ferrous Sulfate, Heptahydrate ($FeSO_4 \cdot 7H_2O$) | mg/L | 13.90 | 13.90 | 13.90 |
| Magnesium Sulfate, Anhydrous ($MgSO_4$) | mg/L | 90.350 | 90.350 | 90.350 |
| Magnesium Sulfate, Monohydrate ($MgSO_4 \cdot H_2O$) | mg/L | 8.450 | 8.450 | 8.450 |
| Molybdic Acid Sodium Salt, Dihydrate ($NaMoO_4 \cdot 2H_2O$) | mg/L | 0.1250 | 0.1250 | 0.1250 |
| Potassium Iodide (KI) | mg/L | 0.4150 | 0.4150 | 0.4150 |
| Potassium Nitrate ($KNO_3$) | mg/L | 950.0 | 950.0 | 950.0 |
| Potassium Phosphate, Monobasic, Anhydrous ($KH_2PO_4$) | mg/L | 85.0 | 85.0 | 85.0 |
| Zinc Sulfate, Heptahydrate ($ZnSO_4 \cdot 7H_2O$) | mg/L | 4.30 | 4.30 | 4.30 |
| Myo-Inositol ($C_6H_5NO_2$) | mg/L | 100.0 | 100.0 | 100.0 |
| Glycine ($C_2H_5NO_2$) | mg/L | 2.0 | 2.0 | 2.0 |
| Nicotinic Acid ($C_6H_5NO_2$) | mg/L | 0.50 | 0.50 | 0.50 |
| Pyridoxine, Hydrochloride ($C_8H_{11}NO_3 \cdot HCL$) | mg/L | 0.50 | 0.50 | 0.50 |
| Thiamine, Hydrochloride ($C_{12}H_{17}ClN_4OS \cdot HCL$) | mg/L | 0.10 | 0.10 | 0.10 |
| Citric Acid | mg/L | 75.0 | 75.0 | 75.0 |
| Ascorbic Acid | mg/L | 75.0 | 75.0 | 75.0 |
| Glutamine | mg/L | 200.0 | 200.0 | 200.0 |
| 2,4-Dichlorophenoxyacetic Acid (2,4-D) | mg/L | — | 1.0 | — |
| N6-(2-Isopentenyl)adenine (2-iP) | mg/L | 2.0 | 3.0 | — |
| 6-Benzylaminopurine (BAP) | mg/L | 1.0 | | 0.1 |
| Kinetin (KIN) | mg/L | | 3.0 | 0.01 |
| 3-Indoleacetic Acid (IAA) | mg/L | — | — | — |
| Naphthaleneacetic Acid (NAA) | mg/L | — | — | 1.0 |
| 2-Naphthoxyacetic acid (NOA) | mg/L | 5.0 | | — |
| Activated Charcoal | g/L | 0.5 | 0.5 | 0.5 |
| Agar, Powder (e.g., Powder Micropropagation Type II - Caisson) | g/L | 7.0 | 7.0 | 7.0 |
| pH | — | 5.7 | 5.7 | 5.7 |

TABLE 11

| Initiation Media VI | | | | | |
|---|---|---|---|---|---|
| Media - Components | Unit | M26 | M28 | M40 | M46 |
| Distilled Water | mL | 990.0 | 990.0 | 990.0 | 990.00 |
| Sucrose | g/L | 30.0 | 30.0 | 30.0 | 30.00 |
| Ammonium Nitrate ($NH_4NO_3$) | mg/L | 825.0 | 1650.0 | 1650.0 | 1650.0 |
| Boric Acid ($H_3BO_3$) | mg/L | 3.10 | 6.20 | 6.20 | 6.20 |
| Calcium Chloride, Anhydrous ($CaCl_2$) | mg/L | 166.050 | 322.10 | 322.10 | 322.10 |
| Cobalt Chloride, Hexahydrate ($CoCl_2 \cdot 6H_2O$) | mg/L | 0.0125 | 0.0250 | 0.0250 | 0.0250 |
| Cupric Sulfate, Pentahydrate ($CuSO_4 \cdot 5H_2O$) | mg/L | 0.0125 | 0.0250 | 0.0250 | 0.0250 |
| EDTA, Disodium, Dihydrate ($C_{10}H_{14}N_2Na_2O_8 \cdot 2H_2O$) | mg/L | 18.630 | 37.260 | 37.260 | 37.260 |
| Ferrous Sulfate, Heptahydrate ($FeSO_4 \cdot 7H_2O$) | mg/L | 13.90 | 27.80 | 27.80 | 27.80 |
| Magnesium Sulfate, Anhydrous ($MgSO_4$) | mg/L | 90.350 | 180.70 | 180.70 | 180.70 |
| Magnesium Sulfate, Monohydrate ($MgSO_4 \cdot H_2O$) | mg/L | 8.450 | 16.90 | 16.90 | 16.90 |
| Molybdic Acid Sodium Salt, Dihydrate ($NaMoO_4 \cdot 2H_2O$) | mg/L | 0.1250 | 0.250 | 0.250 | 0.250 |
| Potassium Iodide (KI) | mg/L | 0.4150 | 0.4150 | 0.4150 | 0.4150 |
| Potassium Nitrate ($KNO_3$) | mg/L | 950.0 | 1900.0 | 1900.0 | 1900.0 |
| Potassium Phosphate, Monobasic, Anhydrous ($KH_2PO_4$) | mg/L | 85.0 | 170.0 | 170.0 | 170.0 |
| Zinc Sulfate, Heptahydrate ($ZnSO_4 \cdot 7H_2O$) | mg/L | 4.30 | 8.60 | 8.60 | 8.60 |
| Myo-Inositol ($C_6H_5NO_2$) | mg/L | 100.0 | 100.0 | 100.0 | 100.0 |
| Glycine ($C_2H_5NO_2$) | mg/L | 2.0 | 2.0 | 2.0 | 2.0 |
| Nicotinic Acid ($C_6H_5NO_2$) | mg/L | 0.50 | 0.50 | 0.50 | 0.50 |
| Pyridoxine, Hydrochloride ($C_8H_{11}NO_3 \cdot HCL$) | mg/L | 0.50 | 0.50 | 0.50 | 0.50 |
| Thiamine, Hydrochloride ($C_{12}H_{17}ClN_4OS \cdot HCL$) | mg/L | 0.10 | 0.10 | 0.10 | 0.10 |
| Citric Acid | mg/L | 0.00 | 0.00 | 0.00 | 0.00 |
| Ascorbic Acid | mg/L | 50.0 | 50.00 | 0.00 | 0.00 |
| Glutamine | mg/L | 200.0 | 200.0 | 200.0 | 200.0 |
| 2,4-Dichlorophenoxyacetic Acid (2,4-D) | mg/L | — | — | 0.1 | 5.0 |
| N6-(2-Isopentenyl)adenine (2-iP) | mg/L | — | 1.0 | | 0.5 |
| 6-Benzylaminopurine (BAP) | mg/L | 1.0 | 1.0 | — | — |
| Kinetin (KIN) | mg/L | | 1.0 | | |
| 3-Indoleacetic Acid (IAA) | mg/L | — | — | 0.1 | |
| Naphthaleneacetic Acid (NAA) | mg/L | 1.0 | — | 1.0 | 5.0 |

TABLE 11-continued

Initiation Media VI

| Media - Components | Unit | M26 | M28 | M40 | M46 |
|---|---|---|---|---|---|
| 2- Naphthoxyacetic acid (NOA) | mg/L | 1.0 | 0.5 | — | |
| Activated Charcoal | g/L | | 0.5 | | |
| Agar, Powder (e.g., Micropropagation Type II - Caisson) | g/L | 7.0 | 7.0 | 7.0 | 7.0 |
| pH | — | 5.7 | 5.7 | 5.7 | 5.7 |

TABLE 12

Multiplication Media II

| Media - Components | Unit | PAE-13 | PAE-15 | PAE-17 | PAE-19 | PAE-21 |
|---|---|---|---|---|---|---|
| Distilled Water | mL | 990.0 | 990.0 | 990.0 | 990.0 | 990.0 |
| Sucrose | g/L | 30.0 | 30.0 | 30.0 | 30.0 | 30.0 |
| Ammonium Nitrate ($NH_4NO_3$) | mg/L | 825.0 | 825.0 | 825.0 | 1650.0 | 1650.0 |
| Boric Acid ($H_3BO_3$) | mg/L | 3.10 | 3.10 | 3.10 | 6.20 | 6.20 |
| Calcium Chloride, Anhydrous ($CaCl_2$) | mg/L | 166.050 | 166.050 | 166.050 | 322.10 | 322.10 |
| Cobalt Chloride, Hexahydrate ($CoCl_2 \cdot 6H_2O$) | mg/L | 0.0125 | 0.0125 | 0.0125 | 0.0250 | 0.0250 |
| Cupric Sulfate, Pentahydrate ($CuSO_4 \cdot 5H_2O$) | mg/L | 0.0125 | 0.0125 | 0.0125 | 0.0250 | 0.0250 |
| EDTA, Disodium, Dihydrate ($C_{10}H_{14}N_2Na_2O_8 \cdot 2H_2O$) | mg/L | 18.630 | 18.630 | 18.630 | 37.260 | 37.260 |
| Ferrous Sulfate, Heptahydrate ($FeSO_4 \cdot 7H_2O$) | mg/L | 13.90 | 13.90 | 13.90 | 27.80 | 27.80 |
| Magnesium Sulfate, Anhydrous ($MgSO_4$) | mg/L | 90.350 | 90.350 | 90.350 | 180.70 | 180.70 |
| Magnesium Sulfate, Monohydrate ($MgSO_4 \cdot H_2O$) | mg/L | 8.450 | 8.450 | 8.450 | 16.90 | 16.90 |
| Molybdic Acid Sodium Salt, Dihydrate ($NaMoO_4 \cdot 2H_2O$) | mg/L | 0.1250 | 0.1250 | 0.1250 | 0.250 | 0.250 |
| Potassium Iodide (KI) | mg/L | 0.4150 | 0.4150 | 0.4150 | 0.830 | 0.4150 |
| Potassium Nitrate ($KNO_3$) | mg/L | 950.0 | 950.0 | 950.0 | 1900.0 | 1900.0 |
| Potassium Phosphate, Monobasic, Anhydrous ($KH_2PO_4$) | mg/L | 85.0 | 85.0 | 85.0 | 170.0 | 170.0 |
| Zinc Sulfate, Heptahydrate ($ZnSO_4 \cdot 7H_2O$) | mg/L | 4.30 | 4.30 | 4.30 | 8.60 | 8.60 |
| Myo-Inositol ($C_6H_5NO_2$) | mg/L | 100.0 | 100.0 | 100.0 | 100.0 | 100.0 |
| Glycine ($C_2H_5NO_2$) | mg/L | 2.0 | 2.0 | 2.0 | 2.0 | 2.0 |
| Nicotinic Acid ($C_6H_5NO_2$) | mg/L | 0.50 | 0.50 | 0.50 | 0.50 | 0.50 |
| Pyridoxine, Hydrochloride ($C_8H_{11}NO_3 \cdot HCL$) | mg/L | 0.50 | 0.50 | 0.50 | 0.50 | 0.50 |
| Thiamine, Hydrochloride ($C_{12}H_{17}ClN_4OS \cdot HCL$) | mg/L | 0.10 | 0.10 | 0.10 | 0.10 | 0.10 |
| Citric Acid | mg/L | 75.0 | 75.0 | 75.0 | 0.0 | 0.0 |
| Ascorbic Acid | mg/L | 75.0 | 75.0 | 75.0 | 0.0 | 0.0 |
| Glutamine | mg/L | 200.0 | 200.0 | 200.0 | 200.0 | 200.0 |
| 2,4-Dichlorophenoxyacetic Acid (2,4-D) | mg/L | — | — | — | | |
| N6-(2-Isopentenyl)adenine (2-iP) | mg/L | | 1.0 | — | | |
| 6-Benzylaminopurine (BAP) | mg/L | 5.0 | 1.0 | 3.0 | 1.0 | 1.0 |
| Kinetin (KIN) | mg/L | — | 1.0 | | | |
| 3-Indoleacetic Acid (IAA) | mg/L | 1.0 | — | | | — |
| Naphthaleneacetic Acid (NAA) | mg/L | 0.1 | — | 1.0 | | — |
| 2-Naphthoxyacetic acid (NOA) | mg/L | 0.5 | 0.5 | — | | |
| Activated Charcoal | g/L | 0.5 | 0.5 | 0.5 | | 0.5 |
| Agar, Powder (e.g., Powder Micropropagation Type II - Caisson) | g/L | 7.0 | 7.0 | 7.0 | 7.0 | 7.0 |
| pH | — | 5.7 | 5.7 | 5.7 | 5.7 | 5.7 |

TABLE 13

Multiplication Media III

| Media - Components | Unit | M21 | M36 |
|---|---|---|---|
| Distilled Water | mL | 990.0 | 990.0 |
| Sucrose | g/L | 30.0 | 30.0 |
| Ammonium Nitrate ($NH_4NO_3$) | mg/L | 1650.0 | 1650.0 |
| Boric Acid ($H_3BO_3$) | mg/L | 6.20 | 6.20 |
| Calcium Chloride, Anhydrous ($CaCl_2$) | mg/L | 322.10 | 322.10 |
| Cobalt Chloride, Hexahydrate ($CoCl_2 \cdot 6H_2O$) | mg/L | 0.0250 | 0.0250 |
| Cupric Sulfate, Pentahydrate ($CuSO_4 \cdot 5H_2O$) | mg/L | 0.0250 | 0.0250 |
| EDTA, Disodium, Dihydrate ($C_{10}H_{14}N_2Na_2O_8 \cdot 2H_2O$) | mg/L | 37.260 | 37.260 |
| Ferrous Sulfate, Heptahydrate ($FeSO_4 \cdot 7H_2O$) | mg/L | 27.80 | 27.80 |
| Magnesium Sulfate, Anhydrous ($MgSO_4$) | mg/L | 180.70 | 180.70 |
| Magnesium Sulfate, Monohydrate ($MgSO_4 \cdot H_2O$) | mg/L | 16.90 | 16.90 |
| Molybdic Acid Sodium Salt, Dihydrate ($NaMoO_4 \cdot 2H_2O$) | mg/L | 0.250 | 0.250 |
| Potassium Iodide (KI) | mg/L | 0.4150 | 0.8300 |
| Potassium Nitrate ($KNO_3$) | mg/L | 1900.0 | 1900.0 |
| Potassium Phosphate, Monobasic, Anhydrous ($KH_2PO_4$) | mg/L | 170.0 | 170.0 |
| Zinc Sulfate, Heptahydrate ($ZnSO_4 \cdot 7H_2O$) | mg/L | 8.60 | 8.60 |
| Myo-Inositol ($C_6H_5NO_2$) | mg/L | 100.0 | 100.0 |
| Glycine ($C_2H_5NO_2$) | mg/L | 2.0 | 2.0 |
| Nicotinic Acid ($C_6H_5NO_2$) | mg/L | 0.50 | 0.50 |
| Pyridoxine, Hydrochloride ($C_8H_{11}NO_3 \cdot HCL$) | mg/L | 0.50 | 0.50 |
| Thiamine, Hydrochloride ($C_{12}H_{17}ClN_4OS \cdot HCL$) | mg/L | 0.10 | 0.10 |
| Citric Acid | mg/L | 0.00 | 0.00 |
| Ascorbic Acid | mg/L | 0.00 | 0.00 |
| Glutamine | mg/L | 200.0 | 0.00 |
| 2,4-Dichlorophenoxyacetic Acid (2,4-D) | mg/L | | 4.0 |
| N6-(2-Isopentenyl)adenine (2-iP) | mg/L | | 0.5 |
| 6-Benzylaminopurine (BAP) | mg/L | 3.0 | 2.0 |
| Kinetin (KIN) | mg/L | | |
| 3-Indoleacetic Acid (IAA) | mg/L | | |
| Naphthaleneacetic Acid (NAA) | mg/L | 0.1 | 1.0 |
| 2-Naphthoxyacetic acid (NOA) | mg/L | — | 1.0 |
| Activated Charcoal | g/L | | |
| Agar, Powder (e.g., Powder Micropropagation Type II - Caisson) | g/L | 7.0 | 7.0 |
| pH | — | 5.7 | 5.7 |

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventor for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A method for micropropagating a Black Barhee date palm plant, comprising:
    applying an initiation medium in vitro to a Black Barhee date palm explant tissue comprising meristematic cells, until a shoot is initiated, wherein the initiation medium is:
    (a) PAE-1, wherein PAE-1 is at pH 5.7 and consists of distilled water (990.0 mL), sucrose (30.0 g/L), ammonium nitrate ($NH_4NO_3$) (825.0 mg/L), boric acid ($H_3BO_3$) (3.10 mg/L), calcium chloride anhydrous ($CaCl_2$) (166.050 mg/L), cobalt chloride hexahydrate ($CoCl_2.6H_2O$) (0.0125 mg/L), cupric sulfate pentahydrate ($CuSO_4.5H_2O$) (0.0125 mg/L), EDTA disodium dihydrate ($C_{10}H_{14}N_2Na_2O_8.2H_2O$) (18.630 mg/L), ferrous sulfate heptahydrate ($FeSO_4.7H_2O$) (13.90 mg/L), magnesium sulfate anhydrous ($MgSO_4$) (90.350 mg/L), magnesium sulfate monohydrate ($MgSO_4.H_2O$) (8.450 mg/L), molybdic acid sodium salt dihydrate ($NaMoO_4.2H_2O$) (0.1250 mg/L), potassium iodide (KI) (0.4150 mg/L), potassium nitrate ($KNO_3$) (950.0 mg/L), potassium phosphate monobasic anhydrous ($KH_2PO_4$) (85.0 mg/L), zinc sulfate heptahydrate ($ZnSO_4.7H_2O$) (4.30 mg/L), myo-inositol ($C_6H_5NO_2$) (100.0 mg/L), glycine ($C_2H_5NO_2$) (2.0 mg/L), nicotinic acid ($C_6H_5NO_2$) (0.50 mg/L), pyridoxine hydrochloride ($C_8H_{11}NO_3.HCl$) (0.50 mg/L), thiamine hydrochloride ($C_{12}H_{17}ClN_4OS.HCl$) (0.10 mg/L), citric acid (75.0 mg/L), ascorbic acid (75.0 mg/L), glutamine (200.0 mg/L), N6-(2-isopentenyl)adenine (2-iP) (2.0 mg/L), 6-benzylaminopurine (BAP) (1.0 mg/L), 2-naphthoxyacetic acid (NOA) (5.0 mg/L), activated charcoal (0.5 g/L), and agar powder (7.0 g/L); or
    (b) PAE-9, wherein PAE-9 is at pH 5.7 and consists of distilled water (990.0 mL), sucrose (30.0 g/L), ammonium nitrate ($NH_4NO_3$) (825.0 mg/L) boric acid ($H_3BO_3$) (3.10 mg/L) calcium chloride anhydrous ($CaCl_2$) (166.050 mg/L), cobalt chloride hexahydrate ($CoCl_2.6H_2O$) (0.0125 mg/L), cupric sulfate pentahydrate ($CuSO_4.5H_2O$) (0.0125 mg/L), EDTA disodium dihydrate ($C_{10}H_{14}N_2Na_2O_8.2H_2O$) (18.630 mg/L), ferrous sulfate heptahydrate ($FeSO_4.7H_2O$) (13.90 mg/L), magnesium sulfate anhydrous ($MgSO_4$) (90.350 mg/L), magnesium sulfate monohydrate ($MgSO_4.H_2O$) (8.450 mg/L), molybdic acid sodium salt dihydrate ($NaMoO_4.2H_2O$) (0.1250 mg/L), potassium iodide (KI) (0.4150 mg/L), potassium nitrate ($KNO_3$) (950.0 mg/L), potassium phosphate monobasic anhydrous ($KH_2PO_4$) (85.0 mg/L), zinc sulfate heptahydrate ($ZnSO_4.7H_2O$) (4.30 mg/L), myo-inositol ($C_6H_5NO_2$) (100.0 mg/L), glycine ($C_2H_5NO_2$) (2.0 mg/L), nicotinic acid ($C_6H_5NO_2$) (0.50 mg/L), pyridoxine hydrochloride ($C_8H_{11}NO_3.HCl$) (0.50 mg/L), thiamine hydrochloride ($C_{12}H_{17}ClN_4OS.HCl$) (0.10 mg/L), citric acid (75.0 mg/L), ascorbic acid (75.0 mg/L), glutamine (200.0 mg/L), 2,4-dichlorophenoxyacetic acid (2,4-D) (1.0 mg/L), N6-(2-isopentenyl)adenine (2-iP) (3.0 mg/L), kinetin (KIN) (3.0 mg/L), activated charcoal (0.5 g/L), and agar powder (7.0 g/L); or
    (c) PAE-7, wherein PAE-7 is at pH 5.7 and consists of distilled water (990.0 mL), sucrose (30.0 g/L), ammonium nitrate ($NH_4NO_3$) (825.0 mg/L), boric acid ($H_3BO_3$) (3.10 mg/L), calcium chloride anhydrous ($CaCl_2$) (166.050 mg/L), cobalt chloride hexahydrate ($CoCl_2.6H_2O$) (0.0125 mg/L), cupric sulfate pentahydrate ($CuSO_4.5H_2O$) (0.0125 mg/L), EDTA disodium dihydrate ($C_{10}H_{14}N_2Na_2O_8.2H_2O$) (18.630 mg/L), ferrous sulfate heptahydrate ($FeSO_4.7H_2O$) (13.90 mg/L), magnesium sulfate anhydrous ($MgSO_4$) (90.350 mg/L), magnesium sulfate monohydrate ($MgSO_4.H_2O$) (8.450 mg/L), molybdic acid sodium salt dihydrate ($NaMoO_4.2H_2O$) (0.1250 mg/L), potassium iodide (KI) (0.4150 mg/L), potassium nitrate ($KNO_3$) (950.0 mg/L), potassium phosphate monobasic anhydrous ($KH_2PO_4$) (85.0 mg/L), zinc sulfate heptahydrate ($ZnSO_4.7H_2O$) (4.30 mg/L), myo-inositol ($C_6H_5NO_2$) (100.0 mg/L), glycine ($C_2H_5NO_2$) (2.0 mg/L), nicotinic acid ($C_6H_5NO_2$) (0.50 mg/L), pyridoxine hydrochloride ($C_8H_{11}NO_3.HCl$) (0.50 mg/L), thiamine hydrochloride ($C_{12}H_{17}ClN_4OS.HCl$) (0.10 mg/L), citric acid (75.0 mg/L), ascorbic acid (75.0 mg/L), glutamine (200.0 mg/L), 6-benzylaminopurine (BAP) (0.1 mg/L), kinetin (KIN) (0.01 mg/L), naphthaleneacetic acid (NAA) (1.0 mg/L), activated charcoal (0.5 g/L), and agar powder (7.0 g/L);
    applying a multiplication medium in vitro to the initiated shoot, wherein the multiplication medium is:
    (a) PAE-15, wherein PAE-15 is at pH 5.7 and consists of distilled water (990.0 mL), sucrose (30.0 g/L), ammonium nitrate ($NH_4NO_3$) (825.0 mg/L), boric acid ($H_3BO_3$) (3.10 mg/L), calcium chloride anhydrous ($CaCl_2$) (166.050 mg/L), cobalt chloride hexahydrate ($CoCl_2.6H_2O$) (0.0125 mg/L), cupric sulfate pentahydrate ($CuSO_4.5H_2O$) (0.0125 mg/L), EDTA disodium dihydrate ($C_{10}H_{14}N_2Na_2O_8.2H_2O$) (18.630 mg/L), ferrous sulfate heptahydrate ($FeSO_4.7H_2O$) (13.90 mg/L), magnesium sulfate anhydrous ($MgSO_4$) (90.350 mg/L), magnesium sulfate monohydrate ($MgSO_4.H_2O$) (8.450 mg/L), molybdic acid sodium salt dihydrate ($NaMoO_4.2H_2O$) (0.1250 mg/L), potassium iodide (KI) (0.4150 mg/L), potassium nitrate ($KNO_3$) (950.0 mg/L), potassium phosphate monobasic anhydrous ($KH_2PO_4$) (85.0 mg/L), zinc sulfate heptahydrate ($ZnSO_4.7H_2O$) (4.30 mg/L), myo-inositol ($C_6H_5NO_2$) (100.0 mg/L), glycine ($C_2H_5NO_2$) (2.0 mg/L), nicotinic acid ($C_6H_5NO_2$) (0.50 mg/L), pyridoxine hydrochloride ($C_8H_{11}NO_3.HCl$) (0.50 mg/L), thiamine hydrochloride ($C_{12}H_{17}ClN_4OS.HCl$) (0.10 mg/L), citric acid (75.0 mg/L), ascorbic acid (75.0 mg/L), glutamine (200.0 mg/L), N6-(2-isopentenyl)adenine (2-iP) (1.0 mg/L), 6-benzylaminopurine (BAP) (1.0 mg/L), kinetin (KIN) (1.0 mg/L), 2-naphthoxyacetic acid (NOA) (0.5 mg/L), activated charcoal (0.5 g/L), and agar powder (7.0 g/L); or (b) PAE-17, wherein PAE-17 is at pH 5.7 and consists of distilled water (990.0 mL), sucrose (30.0 g/L), ammonium nitrate ($NH_4NO_3$) (825.0 mg/L), boric acid ($H_3BO_3$) (3.10 mg/L), calcium chloride anhydrous ($CaCl_2$)) (166.050 mg/L), cobalt chloride hexahydrate ($CoCl_2.6H_2O$) (0.0125 mg/L), cupric sulfate pentahydrate ($CuSO_4.5H_2O$) (0.0125 mg/L), EDTA disodium dihydrate ($C_{10}H_{14}N_2Na_2O_8.2H_2O$) (18.630 mg/L), ferrous sulfate heptahydrate ($FeSO_4.7H_2O$) (13.90 mg/L), magnesium sulfate anhydrous ($MgSO_4$) (90.350 mg/L), magnesium sulfate monohydrate ($MgSO_4.H_2O$) (8.450 mg/L), molybdic acid sodium salt dihydrate ($NaMoO_4.2H_2O$) (0.1250 mg/L), potassium iodide (KI) (0.4150 mg/L), potassium nitrate ($KNO_3$) (950.0 mg/L), potassium phosphate monobasic anhydrous ($KH_2PO_4$) (85.0 mg/L), zinc sulfate heptahydrate ($ZnSO_4.7H_2O$) (4.30 mg/L), myo-inositol ($C_6H_5NO_2$) (100.0 mg/L), glycine ($C_2H_5NO_2$) (2.0 mg/L), nicotinic acid ($C_6H_5NO_2$) (0.50 mg/L), pyridoxine hydrochloride ($C_8H_{11}NO_3.HCl$) (0.50 mg/L), thiamine hydrochloride ($C_{12}H_{17}ClN_4OS.HCl$) (0.10 mg/L), citric acid (75.0 mg/L), ascorbic acid (75.0 mg/L), glutamine (200.0 mg/L), 6-benzylaminopurine (BAP) (3.0 mg/L), naphthaleneacetic acid (NAA) (1.0 mg/L), activated charcoal (0.5 g/L), and agar powder (7.0 g/L); or (c) PAE-19, wherein PAE-19 is at pH 5.7 and consists of distilled water (990.0 mL), sucrose (30.0 g/L), ammonium nitrate ($NH_4NO_3$) (1650.0 mg/L), boric acid ($H_3BO_3$) (6.20 mg/L), calcium chloride anhydrous ($CaCl_2$) (322.10 mg/L), cobalt chloride hexahydrate ($CoCl_2.6H_2O$) (0.0250 mg/L), cupric sulfate pentahydrate ($CuSO_4.5H_2O$) (0.0250 mg/L), EDTA disodium dihydrate ($C_{10}H_{14}N_2Na_2O_8.2H_2O$) (37.260 mg/L), ferrous sulfate heptahydrate ($FeSO_4.7H_2O$) (27.80 mg/L), magnesium sulfate anhydrous ($MgSO_4$) (180.70 mg/L), magnesium sulfate monohydrate ($MgSO_4.H_2O$) (16.90 mg/L), molybdic acid sodium salt dihydrate ($NaMoO_4.2H_2O$) (0.250 mg/L), potassium iodide (KI) (0.830 mg/L), potassium nitrate ($KNO_3$) (1900.0 mg/L), potassium phosphate monobasic anhydrous ($KH_2PO_4$) (170.0 mg/L), zinc sulfate heptahydrate ($ZnSO_4.7H_2O$) (8.60 mg/L), myo-inositol ($C_6H_5NO_2$) (100.0 mg/L), glycine ($C_2H_5NO_2$) (2.0 mg/L), nicotinic acid ($C_6H_5NO_2$) (0.50 mg/L), pyridoxine hydrochloride ($C_8H_{11}NO_3.HCl$) (0.50 mg/L), thiamine hydrochloride ($C_{12}H_{17}ClN_4OS.HCl$) (0.10 mg/L), glutamine (200.0 mg/L), 6-benzylaminopurine (BAP) (1.0 mg/L), and agar powder (7.0 g/L); or (d) PAE-21, wherein PAE-21 is at pH 5.7 and consists of distilled water (990.0 mL), sucrose (30.0 g/L), ammonium nitrate ($NH_4NO_3$) (1650.0 mg/L), boric acid ($H_3BO_3$) (6.20 mg/L), calcium chloride anhydrous ($CaCl_2$) (322.10 mg/L), cobalt chloride hexahydrate ($CoCl_2.6H_2O$) (0.0250 mg/L), cupric sulfate pentahydrate ($CuSO_4.5H_2O$) (0.0250 mg/L), EDTA disodium dihydrate ($C_{10}H_{14}N_2Na_2O_8.2H_2O$) (37.260 mg/L), ferrous sulfate heptahydrate ($FeSO_4.7H_2O$) (27.80 mg/L), magnesium sulfate anhydrous ($MgSO_4$) (180.70 mg/L), magnesium sulfate monohydrate ($MgSO_4.H_2O$) (16.90 mg/L), molybdic acid sodium salt dihydrate ($NaMoO_4.2H_2O$) (0.250 mg/L), potassium iodide (KI) (0.4150 mg/L), potassium nitrate ($KNO_3$) (1900.0 mg/L), potassium phosphate monobasic anhydrous ($KH_2PO_4$) (170.0 mg/L), zinc sulfate heptahydrate ($ZnSO_4.7H_2O$) (8.60 mg/L), myo-inositol ($C_6H_5NO_2$) (100.0 mg/L), glycine ($C_2H_5NO_2$) (2.0 mg/L), nicotinic acid ($C_6H_5NO_2$) (0.50 mg/L), pyridoxine hydrochloride ($C_8H_{11}NO_3.HCl$) (0.50 mg/L), thiamine hydrochloride ($C_{12}H_{17}ClN_4OS.HCl$) (0.10 mg/L), glutamine (200.0 mg/L), 6-benzylaminopurine (BAP) (1.0 mg/L), activated charcoal (0.5 g/L), and agar powder (7.0 g/L); or (e) M21, wherein M21 is at pH 5.7 and consists of distilled water (990.0 mL), sucrose (30.0 g/L), ammonium nitrate ($NH_4NO_3$) (1650.0 mg/L), boric acid ($H_3BO_3$) (6.20 mg/L), calcium chloride anhydrous ($CaCl_2$) (322.10 mg/L), cobalt chloride hexahydrate ($CoCl_2.6H_2O$) (0.0250 mg/L), cupric sulfate pentahydrate ($CuSO_4.5H_2O$) (0.0250 mg/L), EDTA disodium dihydrate ($C_{10}H_{14}N_2Na_2O_8.2H_2O$) (37.260 mg/L), ferrous sulfate heptahydrate ($FeSO_4.7H_2O$) (27.80 mg/L), magnesium sulfate anhydrous ($MgSO_4$) (180.70 mg/L), magnesium sulfate monohydrate ($MgSO_4.H_2O$) (16.90 mg/L), molybdic acid sodium salt dihydrate ($NaMoO_4.2H_2O$) (0.250 mg/L), potassium iodide (KI) (0.4150 mg/L), potassium nitrate ($KNO_3$) (1900.0 mg/L), potassium phosphate monobasic anhydrous ($KH_2PO_4$) (170.0 mg/L), zinc sulfate heptahydrate ($ZnSO_4.7H_2O$) (8.60 mg/L), myo-inositol ($C_6H_5NO_2$) (100.0 mg/L), glycine ($C_2H_5NO_2$) (2.0 mg/L), nicotinic acid ($C_6H_5NO_2$) (0.50 mg/L), pyridoxine hydrochloride ($C_8H_{11}NO_3.HCl$) (0.50 mg/L), thiamine hydrochloride ($C_{12}H_{17}ClN_4OS.HCl$) (0.10 mg/L), glutamine (200.0 mg/L), 6-benzylaminopurine (BAP) (3.0 mg/L), naphthaleneacetic acid (NAA) (0.1 mg/L), and agar powder (7.0 g/L);

separating a plantlet from the multiplication medium for rooting; and inserting the plantlet into a rooting medium so as to obtain the Black Barhee date palm plant.

2. The method of claim 1, wherein the Black Barhee date palm plant is a male.

3. The method of claim 1, wherein the Black Barhee date palm plant is a female.

4. The method of claim 1, wherein the Black Barhee date palm explant tissue comprises plant tissue from an offshoot of a Black Barhee date palm plant.

5. The method of claim 1, wherein the rooting medium is:
(a) M70, wherein M70 consists of ammonium nitrate ($NH_4NO_3$) (1,650 mg/L±2 mg/L), calcium chloride ($CaCl_2$ $2H_2O$) (440 mg/L±2 mg/L), magnesium sulphate ($MgSO_4$ $7H_2O$) (370 mg/L±2 mg/L), potassium phosphate ($KH_2PO_4$) (170 mg/L±2 mg/L), potassium nitrate ($KNO_3$) (1,900 mg/L±2 mg/L), boric acid ($H_3BO_3$) (6.2 mg/L±0.2 mg/L), cobalt chloride ($CoCl_2$ $6H_2O$) (0.025 mg/L±0.002 mg/L), cupric sulphate ($CuSO_4$ $5H_2O$) (0.025 mg/L±0.002 mg/L), ferrous sulphate ($FeSO_4$ $7H_2O$) (27.8 mg/L±0.2 mg/L), manganese sulphate ($MnSO_4$ $4H_2O$) (22.3 mg/L±2 mg/L), potassium iodide (KI) (0.83 mg/L±0.02 mg/L), sodium molybdate ($Na_2MoO_4$ $2H_2O$) (0.25 mg/L±0.02 mg/L), zinc sulphate ($ZnSO_4$ $7H_2O$) (8.6 mg/L±0.2 mg/L), ethylenediaminetetraacetic acid (Na$_2$EDTA 2H$_2$O) (37.2 mg/L±2 mg/L), myo-inositol (100 mg/L±2 mg/L), thiamine (0.4 mg/L±0.3 mg/L), pyridoxine (0.5 mg/L±0.2 mg/L), nicotinic acid (0.5 mg/L±0.2 mg/L), glycine (2 mg/L±0.5 mg/L), sucrose (30 g/L±2 g/L), naphthaleneacetic acid (NAA) (1 mg/L±0.2 mg/L), and agar (1.5 g/L±0.2 g/L); or (b) M82, wherein M82 consists of ammonium nitrate (NH$_4$NO$_3$) (1,650 mg/L±2 mg/L), calcium chloride (CaCl$_2$ 2H$_2$O) (440 mg/L±2 mg/L), magnesium sulphate (MgSO$_4$ 7H$_2$O) (370 mg/L±2 mg/L), potassium phosphate (KH$_2$PO$_4$) (170 mg/L±2 mg/L), potassium nitrate (KNO$_3$) (1,900 mg/L±2 mg/L), boric acid (H$_3$BO$_3$) (6.2 mg/L±0.2 mg/L), cobalt chloride (CoCl$_2$ 6H$_2$O) (0.025 mg/L±0.002 mg/L), cupric sulphate (CuSO$_4$ 5H$_2$O) (0.025 mg/L±0.002 mg/L), ferrous sulphate (FeSO$_4$ 7H$_2$O) (27.8 mg/L±0.2 mg/L), manganese sulphate (MnSO$_4$ 4H$_2$O) (22.3 mg/L±2 mg/L), potassium iodide (KI) (0.83 mg/L±0.02 mg/L), sodium molybdate (Na$_2$MoO$_4$ 2H$_2$O) (0.25 mg/L±0.02 mg/L), zinc sulphate (ZnSO$_4$ 7H$_2$O) (8.6 mg/L±0.2 mg/L), ethylenediaminetetraacetic acid (Na$_2$EDTA 2H$_2$O) (37.2 mg/L±2 mg/L), myo-inositol (100 mg/L±2 mg/L), thiamine (0.4 mg/L±0.3 mg/L), pyridoxine (0.5 mg/L±0.2 mg/L), nicotinic acid (0.5 mg/L±0.2 mg/L), glycine (2 mg/L±0.5 mg/L), sucrose (30 g/L±2 g/L), naphthaleneacetic acid (NAA) (0.1 mg/L±0.02 mg/L), and charcoal (500 mg/L±50 mg/L).

6. The method of claim 1, further comprising treating the Black Barhee date palm explant tissue with antioxidant solution; and sterilizing the Black Barhee date palm explant tissue by gas sterilization after treatment with antioxidant solution.

7. The method of claim 6, wherein the antioxidant solution includes 50-200 mg/L of ascorbic acid and/or citric acid.

8. The method of claim 6, wherein the gas sterilization is carried out in a closed container in which chlorine gas is released through the reaction of bleach with concentrated hydrochloric acid.

9. The method of claim 6, wherein the gas sterilization is for 5-240, 10-120, 20-60 or 30-40 minutes.

10. The method of claim 6, further comprising treating the Black Barhee date palm explant tissue with sodium hypochloride after gas sterilization.

* * * * *